US007662586B2

(12) United States Patent
Monaci et al.

(10) Patent No.: US 7,662,586 B2
(45) Date of Patent: Feb. 16, 2010

(54) SYNTHETIC GENE ENCODING HUMAN EPIDERMAL GROWTH FACTOR 2/NEU ANTIGEN AND USES THEREOF

(75) Inventors: Paolo Monaci, Rome (IT); Pasquale Gallo, Promezia (IT); Maurizio Nuzzo, Rome (IT)

(73) Assignee: Instituto di Ricerche di Biologia Molecolare P. Angeletti S.p.A., Pomezia (Rome) (IT)

( * ) Notice: Subject to any disclaimer, the term of this patent is extended or adjusted under 35 U.S.C. 154(b) by 0 days.

(21) Appl. No.: 12/291,886

(22) Filed: Nov. 14, 2008

(65) Prior Publication Data

US 2009/0098604 A1    Apr. 16, 2009

Related U.S. Application Data

(63) Continuation of application No. 10/565,418, filed as application No. PCT/EP2004/008234 on Jul. 20, 2004, now abandoned.

(60) Provisional application No. 60/489,237, filed on Jul. 21, 2003.

(51) Int. Cl.
C12P 21/06    (2006.01)
C12N 15/00   (2006.01)
C12N 5/00    (2006.01)
C07H 21/04   (2006.01)

(52) U.S. Cl. ............... 435/69.1; 435/320.1; 435/325; 536/23.5

(58) Field of Classification Search ............. None
See application file for complete search history.

(56) References Cited

U.S. PATENT DOCUMENTS

| 5,837,523 A | 11/1998 | Greene et al. |
| 5,846,538 A | 12/1998 | Cheever et al. |
| 5,869,445 A | 2/1999  | Cheever et al. |
| 6,127,344 A | 10/2000 | Amici et al. |

FOREIGN PATENT DOCUMENTS

| WO | WO02/22080 A3   | 3/2002 |
| WO | WO2004/041065 A2 | 5/2004 |
| WO | WO2004/061105 A1 | 7/2004 |

OTHER PUBLICATIONS

Bargmann, et al., "The neu oncogene encodes an epidermal growth factor receptor-related protein", Nature, vol. 319, Jan. 16, 1986, pp. 226-230.
Ben-Levy, et al., "A single autophosphorylation site confers oncogenicity to the Neu/ErbB-2 receptor and enables coupling to the MAP kinase pathway", EMBO Journal, vol. 13, No. 14, pp. 3302-3311, 1994.
Coussens, et al., "Tyrosine Kinase Receptor with Extensive Homology to EGF Receptor Shares Chromosomal Location with neu Oncogene", Science, vol. 230, pp. 1132-1139, Dec. 6, 1985.
Disbrow, et al., "Codon optimization of the HPV-16 E5 gene enhances protein expression", Virology, vol. 311, pp. 105-114, 2003.
Disis, et al., "Cancer Vaccines Targeting the Her2/neu Oncogenic Protein", Seminars in Oncology, vol. 28, No. 6, Suppl. 18, Dec. 2001, pp. 12-20.
Disis, et al., "Generation of T-Cell Immunity to the Her-2/neu Protein After Active Immunication With Her-2/neu Peptide-Based Vaccines", Journal of Clinical Oncology, vol. 20, No. 11, Jun. 1, 2002, pp. 2624-2632.
Disis, et al., "Her-2/neu Protein: A Target for Antigen-Specific Imunotherapy of Human Cancer", Advances in Cancer Research, vol. 71, pp. 343-371, 1997.
Disis, et al., "Oncogene proteins as tumor antigens", Current Opinion in Immunology, vol. 8, 1996, pp. 637-642.
Fisk, et al., "Identification of Naturally Processed Human Ovarian Peptides Recognized by Tumor-Associated CD8+ Cytotoxic T Lymphocytes", Cancer Research, vol. 57, pp. 87-93, Jan. 1, 1997.
Foy, et al., "Vaccination with Her-2/neu DNA or protein subunits protects against growth of a Her-2/neu-expressing murine tumor", Vaccine, vol. 19, pp. 2598-2606, 2001.
Gallo, et al., "Xenogeneic Immunization in Mice Using HER2 DNA Delivered by an Adenoviral Vector", Int. J. Cancer, vol. 113, pp. 67-77, 2004.
Ikemura, "Codon Usage and tRNA Content in Unicellular and Multicellular Organisms", Mol Biol. Evol. vol. 2, No. 1, pp. 13-34, 1985.
Ioannides, et al., "Cytotixic T Cells Isolated from Ovarian Malignant Ascites Recognize a Peptide Derived from the Her-2/neu Protooncogene", Cellular Immunology, vol. 151, pp. 225-235, 1993.
King, et al., "Amplification of a Novel v-erbB-Related Gene in a Human Mammary Carcinoma", Science, vol. 229, No. 4717, pp. 974-976, 1985.
Klapper, et al., "Biochemical and Clinical Implications of the ErbB/HER Signaling Network of Growth Factor Receptors", Adv. Cancer Res., vol. 77, pp. 25-79, 2000.
Leder, et al., "Enhancement of Capsid Gene Expression: Preparing the Human Papillomavirus Type 16 Major Structural Gene L1 for DNA Vaccination Purposes", J. of Virol., vol. 75, No. 19, pp. 9201-9209, Oct. 2001.

(Continued)

Primary Examiner—Marianne P Allen
(74) Attorney, Agent, or Firm—Alysia A. Finnegan; Sheldon O. Heber

(57) ABSTRACT

Synthetic polynucleotides encoding human HER2/neu or a truncated form thereof, are provided, the synthetic polynucleotides being codon-optimized for expression in a human cellular environment. The gene encoding hHER2 is commonly associated with the development of human carcinomas. The present invention provides compositions and methods to elicit or enhance immunity to the protein product expressed by the hHER2 tumor-associated antigen, wherein aberrant hHER2 expression is associated with a carcinoma or its development. This invention specifically provides adenoviral vector and plasmid constructs carrying codon-optimized human HER2 and codon-optimized truncated HER2, and discloses their use in vaccines and pharmaceutical compositions for preventing and treating cancer.

4 Claims, 10 Drawing Sheets

OTHER PUBLICATIONS

Lustgarten, et al., "Identification of Her-2/Neu CTL Epitopes Using Double Transgenic Mice Expressing HLA-A2.1 and Human CD.8", Human Immunology, vol. 52, pp. 109-118, 1997.

Messerle, et al., "NIH/3T3 cells transformed with the activated erbB-2 oncogene can be phenotypically reverted by a kinase deficient, dominant negative erbB-2 variant", Mol. and Cell. Endo., vol. 105, pp. 1-10, 1994.

Montgomery, et al., "Heterologous and Homologous Protection Against Influenza A by DNA Vaccination: Optimization of DNA Vectors", DNA and Cell Biology, vol. 13, No. 9, pp. 777-783, 1993.

Nakamura, et al., "Codon usage tabulated from the international DNA sequence databases: Its status 1999", Nucleic Acids Research, vol. 27, No. 1, pp. 292, 1999.

Peoples, et al., "T lymphocytes that infiltrate tumors and atherosclerotic plaques produce heparin-binding epidermal frowth factor-like growth factor and basic fibroblast growth factor: A potential pathologic role", PNAS, USA, vol. 92, pp. 6547-6551, 1995.

Press, et al., "Expression of the HER-2/neu proto-oncogene in normal human adult and fetal tissues", Oncogene, vol. 5, pp. 953-962, 1990.

Shih, et al., "Transforming genes of carcinomas and neuroblastomas introduced into mouse fibroblasts", Nature, vol. 290, pp. 261-264, Mar. 19, 1981.

Slamon, et al., "Studies of the HER-2/neu Proto-oncogene in Human Breast and Ovarian Cancer", Science, vol. 244, 707-712, May 12, 1989.

Slichenmyer, et al., "Anticancer Therapy Targeting the ErbB Family of Receptor Tyrosine Kinases", Seminars in Oncology, vol. 28, No. 5, Suppl. 16, Oct. 2001, pp. 67-79.

Yamamoto, et al., "Similarity of protein encoded by the human c-erb-B-2 gene to epidermal growth factor receptor", Nature, vol. 319, pp. 230-234, Jan. 22, 1986.

Yarden, et al., "Biology of HER2 and Its Importance in Breast Cancer", Oncology, vol. 61 (Suppl. 2), pp. 1-13, 2001.

Yoshino, et al., "HER2/neu-derived Peptides Are Shared Antigens among Human Non-Small Cell Lung Cancer and Ovarian Cancer", Cancer Research, vol. 54, pp. 3387-3390, 1994.

Human Codon-Optimized HER2/neu Nucleotide Sequence

```
   1 ATGGAGCTGG CCGCCCTGTG CCGCTGGGGC CTGCTGCTGG CCCTGCTGCC
  51 CCCCGGCGCC GCCAGCACCC AGGTGTGCAC CGGCACCGAC ATGAAGCTGC
 101 GCCTGCCCGC CAGCCCCGAG ACCCACCTGG ACATGCTGCG CCACCTGTAC
 151 CAGGGCTGCC AGGTGGTGCA GGGCAACCTG GAGCTGACCT ACCTGCCCAC
 201 CAACGCCAGC CTGAGCTTCC TGCAGGACAT CCAGGAGGTG CAGGGCTACG
 251 TGCTGATCGC CCACAACCAG GTGCGCCAGG TGCCCCTGCA GCGCCTGCGC
 301 ATCGTGCGCG GCACCCAGCT GTTCGAGGAC AACTACGCCC TGGCCGTGCT
 351 GGACAACGGC GACCCCCTGA ACAACACCAC CCCCGTGACC GGCGCCAGCC
 401 CCGGCGGCCT GCGCGAGCTG CAGCTGCGCA GCCTGACCGA GATCCTGAAG
 451 GGCGGCGTGC TGATCCAGCG CAACCCCCAG CTGTGCTACC AGGACACCAT
 501 CCTGTGGAAG GACATCTTCC ACAAGAACAA CCAGCTGGCC CTGACCCTGA
 551 TCGACACCAA CCGCAGCCGC GCCTGCCACC CCTGCAGCCC CATGTGCAAG
 601 GGCAGCCGCT GCTGGGGCGA GAGCAGCGAG GACTGCCAGA GCCTGACCCG
 651 CACCGTGTGC GCCGGCGGCT GCGCCCGCTG CAAGGGCCCC CTGCCCACCG
 701 ACTGCTGCCA CGAGCAGTGC GCCGCCGGCT GCACCGGCCC CAAGCACAGC
 751 GACTGCCTGG CCTGCCTGCA CTTCAACCAC AGCGGCATCT GCGAGCTGCA
 801 CTGCCCCGCC CTGGTGACCT ACAACACCGA CACCTTCGAG AGCATGCCCA
 851 ACCCCGAGGG CCGCTACACC TTCGGCGCCA GCTGCGTGAC CGCCTGCCCC
 901 TACAACTACC TGAGCACCGA CGTGGGCAGC TGCACCCTGG TGTGCCCCCT
 951 GCACAACCAG GAGGTGACCG CCGAGGACGG CACCCAGCGC TGCGAGAAGT
1001 GCAGCAAGCC CTGCGCCCGC GTGTGCTACG GCCTGGGCAT GGAGCACCTG
1051 CGCGAGGTGC GCGCCGTGAC CAGCGCCAAC ATCCAGGAGT TCGCCGGCTG
1101 CAAGAAGATC TTCGGCAGCC TGGCCTTCCT GCCCGAGAGC TTCGACGGCG
1151 ACCCCGCCAG CAACACCGCC CCCCTGCAGC CCGAGCAGCT GCAGGTGTTC
1201 GAGACCCTGG AGGAGATCAC CGGCTACCTG TACATCAGCG CCTGGCCCGA
1251 CAGCCTGCCC GACCTGAGCG TGTTCCAGAA CCTGCAGGTG ATCCGCGGCC
1301 GCATCCTGCA CAACGGCGCC TACAGCCTGA CCCTGCAGGG CCTGGGCATC
1351 AGCTGGCTGG GCCTGCGCAG CCTGCGCGAG CTGGGCAGCG GCCTGGCCCT
1401 GATCCACCAC AACACCCACC TGTGCTTCGT GCACACCGTG CCCTGGGACC
1451 AGCTGTTCCG CAACCCCCAC CAGGCCCTGC TGCACACCGC CAACCGCCCC
1501 GAGGACGAGT GCGTGGGCGA GGGCCTGGCC TGCCACCAGC TGTGCGCCCG
1551 CGGCCACTGC TGGGGCCCCG CCCCCACCCA GTGCGTGAAC TGCAGCCAGT
1601 TCCTGCGCGG CCAGGAGTGC GTGGAGGAGT GCCGCGTGCT GCAGGGCCTG
1651 CCCCGCGAGT ACGTGAACGC CCGCCACTGC CTGCCCTGCC ACCCCGAGTG
1701 CCAGCCCCAG AACGGCAGCG TGACCTGCTT CGGCCCCGAG GCCGACCAGT
1751 GCGTGGCCTG CGCCCACTAC AAGGACCCCC CCTTCTGCGT GGCCCGCTGC
1801 CCCAGCGGCG TGAAGCCCGA CCTGAGCTAC ATGCCCATCT GGAAGTTCCC
```

FIG.1A

```
1851 CGACGAGGAG GGCGCCTGCC AGCCCTGCCC CATCAACTGC ACCCACAGCT
1901 GCGTGGACCT GGACGACAAG GGCTGCCCCG CCGAGCAGCG CGCCAGCCCC
1951 CTGACCAGCA TCATCAGCGC CGTGGTGGGC ATCCTGCTGG TGGTGGTGCT
2001 GGGCGTGGTG TTCGGCATCC TGATCAAGCG CCGCCAGCAG AAGATCCGCA
2051 AGTACACCAT GCGCCGCCTG CTGCAGGAGA CCGAGCTGGT GGAGCCCCTG
2101 ACCCCCAGCG GCGCCATGCC CAACCAGGCC CAGATGCGCA TCCTGAAGGA
2151 GACCGAGCTG CGCAAGGTGA AGGTGCTGGG CAGCGGCGCC TTCGGCACCG
2201 TGTACAAGGG CATCTGGATC CCCGACGGCG AGAACGTGAA GATCCCCGTG
2251 GCCATCGCCG TGCTGCGCGA GAACACCAGC CCCAAGGCCA CAAGGAGAT
2301 CCTGGACGAG GCCTACGTGA TGGCCGGCGT GGGCAGCCCC TACGTGAGCC
2351 GCCTGCTGGG CATCTGCCTG ACCAGCACCG TGCAGCTGGT GACCCAGCTG
2401 ATGCCCTACG GCTGCCTGCT GGACCACGTG CGCGAGAACC GCGGCCGCCT
2451 GGGCAGCCAG GACCTGCTGA ACTGGTGCAT GCAGATCGCC AAGGGCATGA
2501 GCTACCTGGA GGACGTGCGC CTGGTGCACC GCGACCTGGC CGCCCGCAAC
2551 GTGCTGGTGA AGAGCCCCAA CCACGTGAAG ATCACCGACT TCGGCCTGGC
2601 CCGCCTGCTG GACATCGACG AGACCGAGTA CCACGCCGAC GGCGGCAAGG
2651 TGCCCATCAA GTGGATGGCC CTGGAGAGCA TCCTGCGCCG CCGCTTCACC
2701 CACCAGAGCG ACGTGTGGAG CTACGGCGTG ACCGTGTGGG AGCTGATGAC
2751 CTTCGGCGCC AAGCCCTACG ACGGCATCCC CGCCCGCGAG ATCCCCGACC
2801 TGCTGGAGAA GGGCGAGCGC CTGCCCCAGC CCCCCATCTG CACCATCGAC
2851 GTGTACATGA TCATGGTGAA GTGCTGGATG ATCGACAGCG AGTGCCGCCC
2901 CCGCTTCCGC GAGCTGGTGA GCGAGTTCAG CCGCATGGCC CGCGACCCCC
2951 AGCGCTTCGT GGTGATCCAG AACGAGGACC TGGGCCCCGC CAGCCCCCTG
3001 GACAGCACCT TCTACCGCAG CCTGCTGGAG GACGACGACA TGGGCGACCT
3051 GGTGGACGCC GAGGAGTACC TGGTGCCCCA GCAGGGCTTC TTCTGCCCCG
3101 ACCCCGCCCC CGGCGCCGGC GGCATGGTGC ACCACCGCCA CCGCAGCAGC
3151 AGCACCCGCA GCGGCGGCGG CGACCTGACC CTGGGCCTGG AGCCCAGCGA
3201 GGAGGAGGCC CCCCGCAGCC CCCTGGCCCC CAGCGAGGGC GCCGGCAGCG
3251 ACGTGTTCGA CGGCGACCTG GGCATGGGCG CCGCCAAGGG CCTGCAGAGC
3301 CTGCCCACCC ACGACCCCAG CCCCCTGCAG CGCTACAGCG AGGACCCCAC
3351 CGTGCCCCTG CCCAGCGAGA CCGACGGCTA CGTGGCCCCC CTGACCTGCA
3401 GCCCCCAGCC CGAGTACGTG AACCAGCCCG ACGTGCGCCC CCAGCCCCCC
3451 AGCCCCCGCG AGGGCCCCCT GCCGCCGCC CGCCCCGCCG GCGCCACCCT
3501 GGAGCGCCCC AAGACCCTGA GCCCCGGCAA GAACGGCGTG GTGAAGGACG
3551 TGTTCGCCTT CGGCGGCGCC GTGGAGAACC CCGAGTACCT GACCCCCCAG
3601 GGCGGAGCTG CTCCTCAGCC TCACCCTCCA CCTGCTTTCA GCCCTGCTTT
3651 CGACAACCTG TACTACTGGG ACCAGGACCC TCCTGAGAGG GGTGCTCCTC
3701 CTAGCACCTT CAAGGGCACC CCCACCGCCG AGAACCCCGA GTACCTGGGC
3751 CTGGACGTGC CCGTGTAA
(SEQ ID NO:1)
```

FIG.1A-1

Human HER2/neu Protein Sequence

```
   1 MELAALCRWG LLLALLPPGA ASTQVCTGTD MKLRLPASPE THLDMLRHLY QGCQVVQGNL
  61 ELTYLPTNAS LSFLQDIQEV QGYVLIAHNQ VRQVPLQRLR IVRGTQLFED NYALAVLDNG
 121 DPLNNTTPVT GASPGGLREL QLRSLTEILK GGVLIQRNPQ LCYQDTILWK DIFHKNNQLA
 181 LTLIDTNRSR ACHPCSPMCK GSRCWGESSE DCQSLTRTVC AGGCARCKGP LPTDCCHEQC
 241 AAGCTGPKHS DCLACLHFNH SGICELHCPA LVTYNTDTFE SMPNPEGRYT FGASCVTACP
 301 YNYLSTDVGS CTLVCPLHNQ EVTAEDGTQR CEKCSKPCAR VCYGLGMEHL REVRAVTSAN
 361 IQEFAGCKKI FGSLAFLPES FDGDPASNTA PLQPEQLQVF ETLEEITGYL YISAWPDSLP
 421 DLSVFQNLQV IRGRILHNGA YSLTLQGLGI SWLGLRSLRE LGSGLALIHH NTHLCFVHTV
 481 PWDQLFRNPH QALLHTANRP EDECVGEGLA CHQLCARGHC WGPGPTQCVN CSQFLRGQEC
 541 VEECRVLQGL PREYVNARHC LPCHPECQPQ NGSVTCFGPE ADQCVACAHY KDPPFCVARC
 601 PSGVKPDLSY MPIWKFPDEE GACQPCPINC THSCVDLDDK GCPAEQRASP LTSIISAVVG
 661 ILLVVVLGVV FGILIKRRQQ KIRKYTMRRL LQETELVEPL TPSGAMPNQA QMRILKETEL
 721 RKVKVLGSGA FGTVYKGIWI PDGENVKIPV AIAVLRENTS PKANKEILDE AYVMAGVGSP
 781 YVSRLLGICL TSTVQLVTQL MPYGCLLDHV RENRGRLGSQ DLLNWCMQIA KGMSYLEDVR
 841 LVHRDLAARN VLVKSPNHVK ITDFGLARLL DIDETEYHAD GGKVPIKWMA LESILRRRFT
 901 HQSDVWSYGV TVWELMTFGA KPYDGIPARE IPDLLEKGER LPQPPICTID VYMIMVKCWM
 961 IDSECRPRFR ELVSEFSRMA RDPQRFVVIQ NEDLGPASPL DSTFYRSLLE DDDMGDLVDA
1021 EEYLVPQQGF FCPDPAPGAG.GMVHHRHRSS STRSGGGDLT LGLEPSEEEA PRSPLAPSEG
1081 AGSDVFDGDL-GMGAAKGLQS.LPTHDPSPLQ RYSEDPTVPL PSETDGYVAP LTCSPQPEYV
1141 NQPDVRPQPP SPREGPLPAA RPAGATLERP KTLSPGKNGV VKDVFAFGGA VENPEYLTPQ
1201 GGAAPQPHPP PAFSPAFDNL YYWDQDPPER GAPPSTFKGT PTAENPEYLG LDVPV*
(SEQ ID NO:2)
```

FIG.1B

IMMUNODOMINANT T-CELL EPITOPES IN HUMAN HER2/neu PROTEIN

| | | IFN-γ ELIspot | | IFN-γ INTRACELLULAR STAINING | | | |
|---|---|---|---|---|---|---|---|
| | | | | BALB/c | | NeuT | |
| | | BALB/c | NeuT | CD4⁺ | CD8⁺ | CD4⁺ | CD8⁺ |
| hNeu-1 TO hNeu 30 (aa 1-131) | POOL A | 1,127 | | | | | |
| hNeu-11 TO hNeu-15 (aa 41-71) | SUBPOOL A<sub>III</sub> | 1,291 | | | | | |
| hNeu-16 TO hNeu-20 (aa 61-91) | SUBPOOL A<sub>IV</sub> | 1,057 | | | | | |
| | hNeu15 | 1,095 | 1,289 | 0.27 | 46.35 | 0.25 | 47.78 |
| | hNeu16 | 1,075 | | 0.24 | 42.43 | | |
| | hNeu15.1 | 518 | 674 | 0.15 | 25.67 | 0.15 | 25.70 |
| | hNeu15.2 | 143 | 265 | 0.17 | 1.82 | 0.05 | 3.36 |
| | hNeu15.3 | 1,258 | 1,488 | 0.22 | 48.78 | 0.39 | 47.43 |

57 Q G N L E L T Y L P T N A S L S F L Q
(SEC ID NO:5)

| | | | | | | | |
|---|---|---|---|---|---|---|---|
| hNeu-31 TO hNeu-60 (aa 121-251) | POOL B | 65 | n.t. | | | n.t. | n.t. |
| hNeu-41 TO hNeu-45 (aa 161-191) | SUBPOOL B<sub>III</sub> | 81 | n.t. | | | n.t. | n.t. |
| | hNeu41 | 32 | 30 | 0.35 | 0.23 | 0.36 | 0.24 |
| | hNeu42 | 42 | 35 | 0.47 | 0.23 | 0.34 | 0.23 |

161 L C Y Q D T I L W K D I F H K N N Q L
(SEC ID NO:6)

| | | | | | | | |
|---|---|---|---|---|---|---|---|
| hNeu-301 TO hNeu-311 (aa 1201-1255) | POOL K | 150 | n.t. | | | n.t. | n.t. |
| hNeu-301 TO hNeu-305 (aa 1201-1231) | SUBPOOL K<sub>I</sub> | 165 | n.t. | | | n.t. | n.t. |
| | hNeu301 | 128 | 114 | 0.24 | 3.04 | 0.17 | 5.71 |

1202 G G A A P Q P H P P P A F S P
(SEC ID NO:7)

| | | | | | | | |
|---|---|---|---|---|---|---|---|
| DMSO | | | | 0.10 | 0.12 | 0.18 | 0.17 |
| SEB | | | | 1.04 | 2.07 | 1.11 | 1.56 |

FIG.2

IMMUNE RESPONSE TO HUMAN HER2

| MOUSE IFNγELISPOT | | PEPTIDE | |
|---|---|---|---|
| | MOUSE# | hNeu15.3 (CD8+) | hNeu42 (CD4+) |
| pV1J_hHER2.wt | 14, 17 | 15 | 2 |
| pV1J_hHER2.opt | 1, 8 | 286 | 48 |
| pV1J_hHER2wt | 3, 7 | 28 | 16 |
| pV1J_hHER2.opt | 2, 5 | 250 | 60 |

FIG.4A

IMMUNE RESPONSE TO HUMAN HER2

ISOTYPING ANTI-humHER2 Ab

| | IgG1 | IgG2a |
|---|---|---|
| pV1J_hHER2.wt | <100 | <100 |
| pV1J_hHER2.opt | 45,940 | 77,648 |

FIG.4B

IMMUNIZATION OF MICE WITH pV1J-HER2 AND Ad5-hHER2

| | Ad5-hHER2 | | pV1J-hHER2 w/ES | |
|---|---|---|---|---|
| | BALB/c | NeuT | BALB/c | NeuT |
| hNeu15.3 | 1,258 | 1,488 | 41 | 56 |
| hNeu41 | 32 | 30 | 1 | 2 |
| hNeu301 | 128 | 114 | 37 | 30 |

FIG.5

Human Codon-Optimized HER2ECDTM Nucleotide Sequence

```
ATGGAGCTGG CCGCCCTGTG CCGCTGGGGC CTGCTGCTGG CCCTGCTGCC CCCCGGCGCC
GCCAGCACCC AGGTGTGCAC CGGCACCGAC ATGAAGCTGC GCCTGCCCGC CAGCCCCGAG
ACCCACCTGG ACATGCTGCG CCACCTGTAC CAGGGCTGCC AGGTGGTGCA GGGCAACCTG
GAGCTGACCT ACCTGCCCAC CAACGCCAGC CTGAGCTTCC TGCAGGACAT CCAGGAGGTG
CAGGGCTACG TGCTGATCGC CCACAACCAG GTGCGCCAGG TGCCCCTGCA GCGCCTGCGC
ATCGTGCGCG GCACCCAGCT GTTCGAGGAC AACTACGCCC TGGCCGTGCT GGACAACGGC
GACCCCCTGA ACAACACCAC CCCCGTGACC GGCGCCAGCC CCGGCGGCCT GCGCGAGCTG
CAGCTGCGCA GCCTGACCGA GATCCTGAAG GGCGGCGTGC TGATCCAGCG CAACCCCCAG
CTGTGCTACC AGGACACCAT CCTGTGGAAG GACATCTTCC ACAAGAACAA CCAGCTGGCC
CTGACCCTGA TCGACACCAA CCGCAGCCGC GCCTGCCACC CTGCAGCCC CATGTGCAAG
GGCAGCCGCT GCTGGGGCGA GAGCAGCGAG GACTGCCAGA GCCTGACCCG CACCGTGTGC
GCCGGCGGCT GCGCCCGCTG CAAGGGCCCC CTGCCCACCG ACTGCTGCCA CGAGCAGTGC
GCCGCCGGCT GCACCGGCCC CAAGCACAGC GACTGCCTGG CCTGCCTGCA CTTCAACCAC
AGCGGCATCT GCGAGCTGCA CTGCCCCGCC CTGGTGACCT ACAACACCGA CACCTTCGAG
AGCATGCCCA ACCCCGAGGG CCGCTACACC TTCGGCGCCA GCTGCGTGAC CGCCTGCCCC
TACAACTACC TGAGCACCGA CGTGGGCAGC TGCACCCTGG TGTGCCCCCT GCACAACCAG
GAGGTGACCG CCGAGGACGG CACCCAGCGC TGCGAGAAGT GCAGCAAGCC CTGCGCCCGC
GTGTGCTACG GCCTGGGCAT GGAGCACCTG CGCGAGGTGC GCGCCGTGAC CAGCGCCAAC
ATCCAGGAGT TCGCCGGCTG CAAGAAGATC TTCGGCAGCC TGGCCTTCCT GCCCGAGAGC
TTCGACGGCG ACCCCGCCAG CAACACCGCC CCCCTGCAGC CCGAGCAGCT GCAGGTGTTC
GAGACCCTGG AGGAGATCAC CGGCTACCTG TACATCAGCG CCTGGCCCGA CAGCCTGCCC
GACCTGAGCG TGTTCCAGAA CCTGCAGGTG ATCCGCGGCC GCATCCTGCA CAACGGCGCC
TACAGCCTGA CCCTGCAGGG CCTGGGCATC AGCTGGCTGG GCCTGCGCAG CCTGCGCGAG
CTGGGCAGCG GCCTGGCCCT GATCCACCAC AACACCCACC TGTGCTTCGT GCACACCGTG
CCCTGGGACC AGCTGTTCCG CAACCCCCAC CAGGCCCTGC TGCACACCGC CAACCGCCCC
GAGGACGAGT GCGTGGGCGA GGGCCTGGCC TGCCACCAGC TGTGCGCCCG CGGCCACTGC
TGGGGCCCCG GCCCCACCCA GTGCGTGAAC TGCAGCCAGT TCCTGCGCGG CCAGGAGTGC
GTGGAGGAGT GCCGCGTGCT GCAGGGCCTG CCCCGCGAGT ACGTGAACGC CCGCCACTGC
CTGCCCTGCC ACCCCGAGTG CCAGCCCCAG AACGGCAGCG TGACCTGCTT CGGCCCCGAG
GCCGACCAGT GCGTGGCCTG CGCCCACTAC AAGGACCCCC CCTTCTGCGT GGCCCGCTGC
CCCAGCGGCG TGAAGCCCGA CCTGAGCTAC ATGCCCATCT GGAAGTTCCC CGACGAGGAG
GGCGCCTGCC AGCCCTGCCC CATCAACTGC ACCCACAGCT GCGTGGACCT GGACGACAAG
GGCTGCCCCG CCGAGCAGCG CGCCAGCCCC CTGACCAGCA TCATCAGCGC CGTGGTGGGC
ATCCTGCTGG TGGTGGTGCT GGGCGTGGTG TTCGGCATCC TGATCTGA (SEQ ID NO:9)
```

FIG.6A

Human HER2ECDTM wt Nucleotide Sequence

ATGGAGCTG GCGGCCTTG TGCCGCTGG GGCTCCTC CTCGCCCTC TTGCCCCCC GGAGCCGCG
AGCACCCAA GTGTGCACC GGCACAGAC ATGAAGCTG CGGCTCCCT GCCAGTCCC GAGACCCAC
CTGGACATG CTCCGCCAC CTCTACCAG GGCTGCCAG GTGGTGCAG GGAAACCTG GAACTCACC
TACCTGCCC ACCAATGCC AGCCTGTCC TTCCTGCAG GATATCCAG GAGGTGCAG GGCTACGTG
CTCATCGCT CACAACCAA GTGAGGCAG GTCCCACTG CAGAGGCTG CGGATTGTG CGAGGCACC
CAGCTCTTT GAGGACAAC TATGCCCTG GCCGTGCTA GACAATGGA GACCCGCTG AACAATACC
ACCCCTGTC ACAGGGGCC TCCCCAGGA GGCCTGCGG GAGCTGCAG CTTCGAAGC CTCACAGAG
ATCTTGAAA GGAGGGGTC TTGATCCAG CGGAACCCC AGCTCTGC TACCAGGAC ACGATTTTG
TGGAAGGAC ATCTTCCAC AAGAACAAC CAGCTGGCT CTCACACTG ATAGACACC AACCGCTCT
CGGGCCTGC CACCCCTGT TCTCCGATG TGTAAGGGC TCCCGCTGC TGGGGAGAG AGTTCTGAG
GATTGTCAG AGCCTGACG CGCACTGTC TGTGCCGGT GGCTGTGCC CGCTGCAAG GGGCCACTG
CCCACTGAC TGCTGCCAT GAGCAGTGT GCTGCCGGC TGCACGGGC CCCAAGCAC TCTGACTGC
CTGGCCTGC CTCCACTTC AACCACAGT GGCATCTGT GAGCTGCAC TGCCCAGCC CTGGTCACC
TACAACACA GACACGTTT GAGTCCATG CCCAATCCC GAGGGCCGG TATACATTC GGCGCCAGC
TGTGTGACT GCCTGTCCC TACAACTAC CTTTCTACG GACGTGGGA TCCTGCACC CTCGTCTGC
CCCCTGCAC AACCAAGAG GTGACAGCA GAGGATGGA ACACAGCGG TGTGAGAAG TGCAGCAAG
CCCTGTGCC CGAGTGTGC TATGGTCTG GGCATGGAG CACTTGCGA GAGGTGAGG GCAGTTACC
AGTGCCAAT ATCCAGGAG TTTGCTGGC TGCAAGAAG ATCTTTGGG AGCCTGGCA TTTCTGCCG
GAGAGCTTT GATGGGGAC CCAGCCTCC AACACTGCC CCGCTCCAG CCAGAGCAG CTCCAAGTG
TTTGAGACT CTGGAAGAG ATCACAGGT TACCTATAC ATCTCAGCA TGGCCGGAC AGCCTGCCT
GACCTCAGC GTCTTCCAG AACCTGCAA GTAATCCGG GGACGAATT CTGCACAAT GGCGCCTAC
TCGCTGACC CTGCAAGGG CTGGGCATC AGCTGGCTG GGGCTGCGC TCACTGAGG GAACTGGGC
AGTGGACTG GCCCTCATC CACCATAAC ACCCACCTC TGCTTCGTG CACACGGTG CCCTGGGAC
CAGCTCTTT CGGAACCCG CACCAAGCT CTGCTCCAC ACTGCCAAC CGGCCAGAG GACGAGTGT
GTGGGCGAG GGCCTGGCC TGCCACCAG CTGTGCGCC CGAGGGCAC TGCTGGGGT CCAGGGCCC
ACCCAGTGT GTCAACTGC AGCCAGTTC CTTCGGGGC CAGGAGTGC GTGGAGGAA TGCCGAGTA
CTGCAGGGG CTCCCCAGG GAGTATGTG AATGCCAGG CACTGTTTG CCGTGCCAC CCTGAGTGT
CAGCCCCAG AATGGCTCA GTGACCTGT TTTGGACCG GAGGCTGAC CAGTGTGTG GCCTGTGCC
CACTATAAG GACCCTCCC TTCTGCGTG GCCCGCTGC CCCAGCGGT GTGAAACCT GACCTCTCC
TACATGCCC ATCTGGAAG TTTCCAGAT GAGGAGGGC GCATGCCAG CCTTGCCCC ATCAACTGC
ACCCACTCC TGTGTGGAC CTGGATGAC AAGGGCTGC CCCGCCGAG CAGAGAGCC AGCCCTCTG
ACGTCCATC ATCTCTGCG GTGGTTGGC ATTCTGCTG GTCGTGGTC TTGGGGGTG GTCTTTGGG
ATCCTCATC TGA (SEQ ID NO:10)

FIG.6B

RHESUS MONKEY IMMUNIZATION STUDIES

| IMMUNIZATION WEEK | DNA 0 | DNA 8 | DNA 12 | DNA 16 | 23 | Ad5 27 | Ad5 31 | 35 | 40 | 44 |
|---|---|---|---|---|---|---|---|---|---|---|
| RI-497 | | | | | | | | | | |
| A | 3 | 0 | 0 | 0 | 10 | n.t. | 3 | 0 | 0 | 0 |
| B | 5 | 0 | 0 | 47 | 20 | n.t. | 3 | 0 | 5 | 0 |
| C | 5 | 15 | 45 | 50 | 60 | n.t. | 0 | 0 | 5 | 0 |
| D | 13 | 20 | 5 | 67 | 47 | n.t. | 10 | 0 | 5 | 0 |
| E | 10 | 0 | 0 | 15 | 25 | n.t. | 5 | 0 | 0 | 0 |
| F | 5 | 0 | 0 | 0 | 17 | n.t. | 13 | 8 | 8 | 0 |
| G | 8 | 0 | 0 | 57 | 20 | n.t. | 15 | 0 | 0 | 0 |
| H | 3 | 20 | 0 | 35 | 30 | n.t. | 0 | 0 | 5 | 0 |
| J | 8 | 0 | 0 | 75 | 37 | n.t. | 3 | 0 | 5 | 0 |
| RI-503 | | | | | | | | | | |
| A | 3 | 18 | 13 | 5 | 8 | n.t. | 3 | 5 | 5 | 0 |
| B | 0 | 13 | 13 | 3 | 5 | n.t. | 3 | 3 | 5 | 0 |
| C | 1 | 10 | 13 | 15 | 8 | n.t. | 3 | 3 | 3 | 3 |
| D | 4 | 8 | 13 | 5 | 8 | n.t. | 0 | 3 | 0 | 0 |
| E | 6 | 10 | 10 | 8 | 3 | n.t. | 3 | 13 | 8 | 18 |
| F | 4 | 13 | 33 | 13 | 10 | n.t. | 20 | 95 | 13 | 10 |
| G | 8 | 8 | 18 | 5 | 8 | n.t. | 0 | 3 | 3 | 0 |
| H | 4 | 15 | 23 | 15 | 10 | n.t. | 5 | 3 | 0 | 0 |
| J | 4 | 13 | 13 | 13 | 5 | n.t. | 3 | 3 | 3 | 0 |
| RI-512 | | | | | | | | | | |
| A | 3 | 0 | 23 | 2 | 0 | n.t. | 0 | 0 | 13 | 0 |
| B | 14 | 0 | 23 | 22 | 0 | n.t. | 43 | 65 | 65 | 15 |
| C | 20 | 0 | 30 | 17 | 3 | n.t. | 53 | 60 | 85 | 8 |
| D | 13 | 0 | 15 | 5 | 0 | n.t. | 0 | 0 | 8 | 0 |
| E | 24 | 0 | 0 | 2 | 0 | n.t. | 23 | 23 | 28 | 8 |
| F | 8 | 0 | 23 | 0 | 20 | n.t. | 303 | 473 | 535 | 145 |
| G | 21 | 0 | 13 | 7 | 0 | n.t. | 0 | 8 | 988 | 183 |
| H | 19 | 3 | 28 | n.t. | 8 | n.t. | n.t. | 10 | 8 | 3 |
| J | 13 | 3 | 0 | n.t. | 13 | n.t. | n.t. | 140 | 128 | 15 |
| RI-520 | | | | | | | | | | |
| A | 3 | 0 | 0 | 15 | 0 | n.t. | 0 | 3 | 2.5 | 0 |
| B | 0 | 3 | 0 | 0 | 0 | n.t. | 0 | 3 | 0 | 0 |
| C | 0 | 0 | 5 | 5 | 0 | n.t. | 3 | 3 | 0 | 0 |
| D | 0 | 8 | 17 | 10 | 7 | n.t. | 0 | 0 | 0 | 0 |
| E | 0 | 0 | 0 | 20 | 0 | n.t. | 33 | 3 | 5 | 35 |
| F | 0 | 5 | 10 | 10 | 0 | n.t. | 10 | 28 | 30 | 54 |
| G | 0 | 3 | 0 | 5 | 0 | n.t. | 0 | 3 | 2.5 | 0 |
| H | 0 | 3 | 0 | 5 | 0 | n.t. | 0 | 5 | 0 | 0 |
| J | 0 | 0 | 2 | 20 | 0 | n.t. | 0 | 0 | 0 | e |

FIG.7

IMMUNIZATION OF MICE WITH pV1J-HER2opt AND pV1J-HER2ECDTM.opt

|                    | hNeu15.3 | hNeu41 |
|--------------------|----------|--------|
| pVIJ-hHER2.opt     | 468      | 12     |
| pVIJ-hHER2ECDTM.opt| 655      | 92     |

FIG.8

SEQUENCE LISTING

<160> NUMBER OF SEQ ID NOS: 14

<210> SEQ ID NO 1
<211> LENGTH: 3768
<212> TYPE: DNA
<213> ORGANISM: Artificial Sequence
<220> FEATURE:
<223> OTHER INFORMATION: HER2opt

<400> SEQUENCE: 1

| | | | | | |
|---|---|---|---|---|---|
| atggagctgg | ccgccctgtg | ccgctggggc | ctgctgctgg | ccctgctgcc | ccccggcgcc | 60 |
| gccagcaccc | aggtgtgcac | cggcaccgac | atgaagctgc | gcctgcccgc | cagccccgag | 120 |
| acccacctgg | acatgctgcg | ccacctgtac | cagggctgcc | aggtggtgca | gggcaacctg | 180 |
| gagctgacct | acctgcccac | caacgccagc | ctgagcttcc | tgcaggacat | ccaggaggtg | 240 |
| cagggctacg | tgctgatcgc | ccacaaccag | gtgcgccagg | tgcccctgca | gcgcctgcgc | 300 |
| atcgtgcgcg | gcacccagct | gttcgaggac | aactacgccc | tggccgtgct | ggacaacggc | 360 |
| gaccccctga | caacaccac | ccccgtgacc | ggcgccagcc | ccggcggcct | gcgcgagctg | 420 |
| cagctgcgca | gcctgaccga | gatcctgaag | ggcggcgtgc | tgatccagcg | caacccccag | 480 |
| ctgtgctacc | aggacaccat | cctgtggaag | gacatcttcc | acaagaacaa | ccagctggcc | 540 |
| ctgaccctga | tcgacaccaa | ccgcagccgc | gcctgccacc | cctgcagccc | catgtgcaag | 600 |
| ggcagccgct | gctggggcga | gagcagcgag | gactgccaga | gcctgacccg | caccgtgtgc | 660 |
| gccggcggct | gcgcccgctg | caagggcccc | ctgcccaccg | actgctgcca | cgagcagtgc | 720 |
| gccgccggct | gcaccggccc | caagcacagc | gactgcctgg | cctgcctgca | cttcaaccac | 780 |
| agcggcatct | gcgagctgca | ctgccccgcc | ctggtgacct | acaacaccga | caccttcgag | 840 |
| agcatgccca | accccgaggg | ccgctacacc | ttcggcgcca | gctgcgtgac | cgcctgcccc | 900 |
| tacaactacc | tgagcaccga | cgtgggcagc | tgcacccggg | tgtgcccccct | gcacaaccag | 960 |
| gaggtgaccg | ccgaggacgg | cacccagcgc | tgcgagaagt | gcagcaagcc | ctgcgcccgc | 1020 |
| gtgtgctacg | gcctgggcat | ggagcacctg | cgcgaggtgc | gcgccgtgac | cagcgccaac | 1080 |
| atccaggagt | cgccggctg | caagaagatc | ttcggcagcc | tggccttcct | gcccgagagc | 1140 |
| ttcgacggcg | accccgccag | caacaccgcc | ccctgcagc | ccgagcagct | gcaggtgttc | 1200 |
| gagaccctgg | aggagatcac | cggctacctg | tacatcagcg | cctggcccga | cagcctgccc | 1260 |
| gacctgagcg | tgttccagaa | cctgcaggtg | atccgcggcc | gcatcctgca | aacggcgcc | 1320 |
| tacagcctga | ccctgcaggg | cctgggcatc | agctggctgg | gcctgcgcag | cctgcgcgag | 1380 |
| ctgggcagcg | gcctggccct | gatccaccac | aacacccacc | tgtgcttcgt | gcacaccgtg | 1440 |
| ccctgggacc | agctgttccg | caacccccac | caggccctgc | tgcacaccgc | caaccgcccc | 1500 |
| gaggacgagt | gcgtgggcga | gggcctggcc | tgccaccagc | tgtgcgcccg | cggccactgc | 1560 |
| tgggcccccg | gcccaccca | gtgcgtgaac | tgcagccagt | cctgcgcggg | ccaggagtgc | 1620 |
| gtggaggagt | gccgcgtgct | gcagggcctg | cccgcgagt | acgtgaacgc | cgccactgc | 1680 |
| ctgccctgcc | accccgagtg | ccagccccag | aacggcagcg | tgacctgctt | cggccccgag | 1740 |
| gccgaccagt | gcgtggcctg | cgcccactac | aaggaccccc | ccttctgcgt | ggcccgctgc | 1800 |
| cccagcggcg | tgaagcccga | cctgagctac | atgcccatct | ggaagttccc | cgacgaggag | 1860 |
| ggcgcctgcc | agccctgccc | catcaactgc | acccacagct | gcgtggacct | ggacgacaag | 1920 |
| ggctgccccg | ccgagcagcg | cgccagcccc | ctgaccagca | tcatcagcgc | cgtggtgggc | 1980 |

-continued

```
atcctgctgg tggtggtgct gggcgtggtg ttcggcatcc tgatcaagcg ccgccagcag    2040
aagatccgca agtacaccat gcgccgcctg ctgcaggaga ccgagctggt ggagcccctg    2100 accccccagcg gcgccatgcc caaccaggcc cagatgcgca tcctgaagga gaccgagctg    2160
cgcaaggtga aggtgctggg cagcggcgcc ttcggcaccg tgtacaaggg catctggatc    2220
cccgacggcg agaacgtgaa gatccccgtg gccatcgccg tgctgcgcga aaacaccagc    2280
cccaaggcca acaaggagat cctggacgag gcctacgtga tggccggcgt gggcagcccc    2340
tacgtgagcc gcctgctggg catctgcctg accagcaccg tgcagctggt gacccagctg    2400
atgccctacg gctgcctgct ggaccacgtg cgcgagaacc gcggccgcct gggcagccag    2460
gacctgctga actggtgcat gcagatcgcc aagggcatga gctacctgga ggacgtgcgc    2520
ctggtgcacc gcgacctggc cgcccgcaac gtgctggtga agagccccaa ccacgtgaag    2580
atcaccgact cggcctggcc cgcctgctg gacatcgacg agaccgagta ccacgccgac    2640
ggcggcaagg tgcccatcaa gtggatggcc ctggagagca tcctgcgccg ccgcttcacc    2700
caccagagcg acgtgtggag ctacggcgtg accgtgtggg agctgatgac cttcggcgcc    2760
aagccctacg acggcatccc cgcccgcgag atccccgacc tgctggagaa gggcgagcgc    2820
ctgccccagc cccccatctg caccatcgac gtgtacatga tcatggtgaa gtgctggatg    2880
atcgacagcg agtgccgccc ccgcttccgc gagctggtga gcgagttcag ccgcatggcc    2940
cgcgaccccc agcgcttcgt ggtgatccag aacgaggacc tgggccccgc cagcccctg    3000 gacagcacct tctaccgcag cctgctggag gacgacgaca tgggcgacct ggtggacgcc    3060
gaggagtacc tggtgcccca gcagggcttc ttctgccccg accccgcccc cggcgccggc    3120
ggcatggtgc accaccgcca ccgcagcagc agcacccgca cgcggcggcg gcacctgacc    3180
ctgggcctgg agcccagcga ggaggaggcc cccgcagcc cctggcccc cagcgagggc    3240 gccggcagcg acgtgttcga cggcgacctg ggcatgggcg ccgccaaggg cctgcagagc    3300
ctgcccaccc acgaccccag ccccctgcag cgctacagcg aggaccccac cgtgcccctg    3360
cccagcgaga ccgacggcta cgtggccccc ctgacctgca gccccagcc cgagtacgtg    3420 aaccagcccg acgtgcgccc ccagcccccc agccccgcg agggccccct gcccgccgcc    3480
cgccccgccg cgccaccct ggagcgcccc aagaccctga ccccggcaa gaacggcgtg    3540 gtgaaggacg tgttcgcctt cggcggcgcc gtggagaacc ccgagtacct gaccccccag    3600
ggcggagctg ctcctcagcc tcaccctcca cctgctttca gccctgcttt cgacaacctg    3660
tactactggg accaggaccc tcctgagagg ggtgctcctc ctagcacctt caagggcacc    3720
cccaccgccg agaaccccga gtacctgggc ctggacgtgc ccgtgtaa               3768
```

<210> SEQ ID NO 2
<211> LENGTH: 1255
<212> TYPE: PRT
<213> ORGANISM: Homo Sapiens, HER2

<400> SEQUENCE: 2

```
Met Glu Leu Ala Ala Leu Cys Arg Trp Gly Leu Leu Ala Leu Leu
  1               5                  10                  15

Pro Pro Gly Ala Ala Ser Thr Gln Val Cys Thr Gly Thr Asp Met Lys
                 20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
```

```
            50                  55                  60
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480
```

-continued

```
Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Ala Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895
```

-continued

```
Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Arg Leu Pro Gln Pro
            930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Ala Gly
1025                1030                1035                1040

Gly Met Val His His Arg His Arg Ser Ser Ser Thr Arg Ser Gly Gly
            1045                1050                1055

Gly Asp Leu Thr Leu Gly Leu Glu Pro Ser Glu Glu Glu Ala Pro Arg
            1060                1065                1070

Ser Pro Leu Ala Pro Ser Glu Gly Ala Gly Ser Asp Val Phe Asp Gly
            1075                1080                1085

Asp Leu Gly Met Gly Ala Ala Lys Gly Leu Gln Ser Leu Pro Thr His
            1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
            1125                1130                1135

Pro Glu Tyr Val Asn Gln Pro Asp Val Arg Pro Gln Pro Pro Ser Pro
            1140                1145                1150

Arg Glu Gly Pro Leu Pro Ala Ala Arg Pro Ala Gly Ala Thr Leu Glu
            1155                1160                1165

Arg Pro Lys Thr Leu Ser Pro Gly Lys Asn Gly Val Val Lys Asp Val
            1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Ala Phe Ser Pro Ala
            1205                1210                1215

Phe Asp Asn Leu Tyr Tyr Trp Asp Gln Asp Pro Pro Glu Arg Gly Ala
            1220                1225                1230

Pro Pro Ser Thr Phe Lys Gly Thr Pro Thr Ala Glu Asn Pro Glu Tyr
            1235                1240                1245

Leu Gly Leu Asp Val Pro Val
            1250                1255

<210> SEQ ID NO 3
<211> LENGTH: 43
<212> TYPE: DNA
<213> ORGANISM: Artificial Sequence
<220> FEATURE:
<223> OTHER INFORMATION: PCR Primer

<400> SEQUENCE: 3
```

```
ccagtttaaa catttaaatg ccgccaccat ggagctggcg gcc         43
```

<210> SEQ ID NO 4
<211> LENGTH: 33
<212> TYPE: DNA
<213> ORGANISM: Artificial Sequence
<220> FEATURE:
<223> OTHER INFORMATION: PCR Primer

<400> SEQUENCE: 4

```
gccgtcgact ttacactggc acgtccagac cca                    33
```

<210> SEQ ID NO 5
<211> LENGTH: 19
<212> TYPE: PRT
<213> ORGANISM: Artificial Sequence
<220> FEATURE:
<223> OTHER INFORMATION: HER2 Peptide

<400> SEQUENCE: 5

Gln Gly Asn Leu Glu Leu Thr Tyr Leu Pro Thr Asn Ala Ser Leu Ser
 1               5                  10                  15

Phe Leu Gln

<210> SEQ ID NO 6
<211> LENGTH: 19
<212> TYPE: PRT
<213> ORGANISM: Artificial Sequence
<220> FEATURE:
<223> OTHER INFORMATION: HER2 Peptide

<400> SEQUENCE: 6

Leu Cys Tyr Gln Asp Thr Ile Leu Trp Lys Asp Ile Phe His Lys Asn
 1               5                  10                  15

Asn Gln Leu

<210> SEQ ID NO 7
<211> LENGTH: 15
<212> TYPE: PRT
<213> ORGANISM: Artificial Sequence
<220> FEATURE:
<223> OTHER INFORMATION: HER2 Peptide

<400> SEQUENCE: 7

Gly Gly Ala Ala Pro Gln Pro His Pro Pro Pro Ala Phe Ser Pro
 1               5                  10                  15

<210> SEQ ID NO 8
<211> LENGTH: 9
<212> TYPE: DNA
<213> ORGANISM: Artificial Sequence
<220> FEATURE:
<223> OTHER INFORMATION: Kozak Sequence

<400> SEQUENCE: 8

```
gccgccacc                                               9
```

<210> SEQ ID NO 9
<211> LENGTH: 2028
<212> TYPE: DNA
<213> ORGANISM: Artificial Sequence
<220> FEATURE:
<223> OTHER INFORMATION: HER2ECDTMopt

<400> SEQUENCE: 9

-continued

```
atggagctgg ccgccctgtg ccgctggggc ctgctgctgg ccctgctgcc ccccggcgcc      60
gccagcaccc aggtgtgcac cggcaccgac atgaagctgc gcctgccgc cagccccgag      120
acccacctgg acatgctgcg ccacctgtac cagggctgcc aggtggtgca gggcaacctg      180
gagctgacct acctgcccac caacgccagc ctgagcttcc tgcaggacat ccaggaggtg      240
cagggctacg tgctgatcgc ccacaaccag gtgcgccagg tgcccctgca gcgcctgcgc      300
atcgtgcgcg gcacccagct gttcgaggac aactacgccc tggccgtgct ggacaacggc      360
gaccccctga caacaccac ccccgtgacc ggcgccagcc ccggcggcct gcgcgagctg      420
cagctgcgca gcctgaccga gatcctgaag ggcggcgtgc tgatccagcg caacccccag      480
ctgtgctacc aggacaccat cctgtggaag gacatcttcc acaagaacaa ccagctggcc      540
ctgaccctga tcgacaccaa ccgcagccgc gcctgccacc cctgcagccc catgtgcaag      600
ggcagccgct gctggggcga gagcagcgag gactgccaga gcctgacccg caccgtgtgc      660
gccggcggct gcgcccgctg caagggcccc ctgcccaccg actgctgcca cgagcagtgc      720
gccgccggct gcaccggccc caagcacagc gactgcctgg cctgcctgca cttcaaccac      780
agcggcatct gcgagctgca ctgccccgcc tggtgacct acaacaccga caccttcgag      840
agcatgccca accccgaggg ccgctacacc ttcggcgcca gctgcgtgac cgcctgcccc      900
tacaactacc tgagcaccga cgtgggcagc tgcaccctgg tgtgcccct gcacaaccag      960
gaggtgaccg ccgaggacgg cacccagcgc tgcgagaagt gcagcaagcc ctgcgcccgc      1020
gtgtgctacg gcctgggcat ggagcacctg cgcgaggtgc gcgccgtgac cagcgccaac      1080
atccaggagt cgccggctg caagaagatc ttcggcagcc tggccttcct gcccgagagc      1140
ttcgacggcg accccgccag caacaccgcc cccctgcagc ccgagcagct gcaggtgttc      1200
gagaccctgg aggagatcac cggctacctg tacatcagcg cctggcccga cagcctgccc      1260
gacctgagcg tgttccagaa cctgcaggtg atccgcggcc gcatcctgca caacggcgcc      1320
tacagcctga ccctgcaggg cctgggcatc agctggctgg gcctgcgcag cctgcgcgag      1380
ctgggcagcg gcctggccct gatccaccac aacacccacc tgtgcttcgt gcacaccgtg      1440
ccctgggacc agctgttccg caacccccac caggccctgc tgcacaccgc caaccgcccc      1500
gaggacgagt gcgtgggcga gggcctggcc tgccaccagc tgtgcgcccg cggccactgc      1560
tggggccccg gccccaccca gtgcgtgaac tgcagccagt tcctgcgcgg ccaggagtgc      1620
gtggaggagt gccgcgtgct gcagggcctc cccgcgagt acgtgaacgc ccgccactgc      1680
ctgccctgcc accccgagtg ccagccccag aacggcagcg tgacctgctt cggccccgag      1740
gccgaccagt gcgtggcctg cgcccactac aaggaccccc ccttctgcgt ggcccgctgc      1800
cccagcggcg tgaagcccga cctgagctac atgcccatct ggaagttccc cgacgaggag      1860
ggcgcctgcc agccctgccc catcaactgc acccacagct gcgtggacct ggacgacaag      1920
ggctgccccg ccgagcagcg cgccagcccc ctgaccagca tcatcagcgc cgtggtgggc      1980
atcctgctgg tggtggtgct gggcgtggtg ttcggcatcc tgatctga              2028
```

<210> SEQ ID NO 10
<211> LENGTH: 2028
<212> TYPE: DNA
<213> ORGANISM: Artificial Sequence
<220> FEATURE:
<223> OTHER INFORMATION: HER2ECDTMwt

<400> SEQUENCE: 10

```
atggagctgg cggccttgtg ccgctggggg ctcctcctcg ccctcttgcc ccccggagcc      60
```

-continued

```
gcgagcaccc aagtgtgcac cggcacagac atgaagctgc ggctccctgc cagtcccgag      120
acccacctgg acatgctccg ccacctctac cagggctgcc aggtggtgca gggaaacctg      180
gaactcacct acctgccac caatgccagc ctgtccttcc tgcaggatat ccaggaggtg       240
cagggctacg tgctcatcgc tcacaaccaa gtgaggcagg tcccactgca gaggctgcgg      300
attgtgcgag caccagct ctttgaggac aactatgccc tggccgtgct agacaatgga       360
gacccgctga caataccac ccctgtcaca ggggcctccc caggaggcct gcgggagctg       420
cagcttcgaa gcctcacaga gatcttgaaa ggaggggtct tgatccagcg gaaccccag       480 ctctgctacc aggacacgat tttgtggaag gacatcttcc acaagaacaa ccagctggct      540
ctcacactga tagacaccaa ccgctctcgg gcctgccacc cctgttctcc gatgtgtaag      600
ggctcccgct gctggggaga gagttctgag gattgtcaga gcctgacgcg cactgtctgt      660
gccggtggct gtgcccgctg caagggccca ctgcccactg actgctgcca tgagcagtgt      720
gctgccggct gcacgggccc caagcactct gactgcctgg cctgcctcca cttcaaccac      780
agtggcatct gtgagctgca ctgcccagcc ctggtcacct acaacacaga cacgtttgag      840
tccatgccca atcccgaggg ccggtataca ttcggcgcca gctgtgtgac tgcctgtccc      900
tacaactacc tttctacgga cgtgggatcc tgcacccctcg tctgccccct gcacaaccaa      960
gaggtgacag cagaggatgg aacacagcgg tgtgagaagt gcagcaagcc ctgtgcccga     1020
gtgtgctatg gtctgggcat ggagcacttg cgagaggtga gggcagttac cagtgccaat     1080
atccaggagt ttgctggctg caagaagatc tttgggagcc tggcatttct gccggagagc     1140
tttgatgggg acccagcctc caacactgcc ccgctccagc cagagcagct ccaagtgttt     1200
gagactctgg aagagatcac aggttaccta tacatctcag catggccgga cagcctgcct     1260
gacctcagcg tcttccagaa cctgcaagta tccggggac gaattctgca caatggcgcc     1320
tactcgctga cccctgcaagg gctgggcatc agctggctgg gctgcgctc actgagggaa     1380 ctgggcagtg gactggccct catccaccat aacacccacc tctgcttcgt gcacacggtg     1440
ccctgggacc agctctttcg gaacccgcac caagctctgc tccacactgc caaccggcca     1500
gaggacgagt gtgtgggcga gggcctggcc tgccaccagc tgtgcgcccg agggcactgc     1560 tgggtccag ggcccaccca gtgtgtcaac tgcagccagt tccttcgggg ccaggagtgc     1620
gtggaggaat gccgagtact gcaggggctc cccagggagt atgtgaatgc aggcactgt     1680 ttgccgtgcc accctgagtg tcagccccag aatggctcag tgacctgttt tggaccggag     1740
gctgaccagt gtgtggcctg tgcccactat aaggaccctc ccttctgcgt ggcccgctgc     1800
cccagcggtg tgaaacctga cctctcctac atgcccatct ggaagtttcc agatgaggag     1860
ggcgcatgcc agccttgccc catcaactgc acccactcct gtgtggacct ggatgacaag     1920
ggctgccccg ccgagcagag agccagccct ctgacgtcca tctctctgcg ggtggttggc     1980
attctgctgg tcgtggtctt gggggtggtc tttgggatcc tcatctga                 2028
```

<210> SEQ ID NO 11
<211> LENGTH: 3778
<212> TYPE: DNA
<213> ORGANISM: Artificial Sequence
<220> FEATURE:
<223> OTHER INFORMATION: hHER2opt + Kozak

<400> SEQUENCE: 11

```
gccgccacca tggagctggc cgccctgtgc cgctggggcc tgctgctggc cctgctgccc     60
```

```
cccggcgccg ccagcaccca ggtgtgcacc ggcaccgaca tgaagctgcg cctgcccgcc      120
agccccgaga cccacctgga catgctgcgc cacctgtacc agggctgcca ggtggtgcag      180
ggcaacctgg agctgaccta cctgccacc aacgccagcc tgagcttcct gcaggacatc      240
caggaggtgc agggctacgt gctgatcgcc cacaaccagg tgcgccaggt gcccctgcag      300
cgcctgcgca tcgtgcgcgg cacccagctg ttcgaggaca actacgccct ggccgtgctg      360
gacaacggcg accccctgaa caacaccacc cccgtgaccg cgccagccc cggcggcctg      420 cgcgagctgc agctgcgcag cctgaccgag atcctgaagg cggcgtgct gatccagcgc      480 aaccccagc tgtgctacca ggacaccatc ctgtggaaga catcttcca caagaacaac      540 cagctggccc tgaccctgat cgacaccaac cgcagccgcg cctgccaccc ctgcagcccc      600
atgtgcaagg gcagccgctg ctggggcgag agcagcgagg actgccagag cctgacccgc      660
accgtgtgcg ccggcggctg cgcccgctgc aagggccccc tgcccaccga ctgctgccac      720
gagcagtgcg ccgccggctg caccggcccc aagcacagcg actgcctggc ctgcctgcac      780
ttcaaccaca gcggcatctg cgagctgcac tgccccgccc tggtgaccta caacaccgac      840
accttcgaga gcatgcccaa ccccgagggc cgctacacct tcggcgccag ctgcgtgacc      900
gcctgcccct acaactacct gagcaccgac gtgggcagct gcaccctggt gtgccccctg      960
cacaaccagg aggtgaccgc cgaggacggc acccagcgct gcgagaagtg cagcaagccc     1020
tgcgcccgcg tgtgctacgg cctgggcatg gagcacctgc gcgaggtgcg cgccgtgacc     1080
agcgccaaca tccaggagtt cgccggctgc aagaagatct cggcagcct ggccttcctg     1140 cccgagagct cgacggcga ccccgccagc aacaccgccc cctgcagcc cgagcagctg     1200 caggtgttcg agaccctgga ggagatcacc ggctacctgt acatcagcgc ctggcccgac     1260
agcctgcccg acctgagcgt gttccagaac ctgcaggtga tccgcggccg catcctgcac     1320
aacggcgcct acagcctgac cctgcagggc ctgggcatca gctggctggg cctgcgcagc     1380
ctgcgcgagc tgggcagcgg cctggccctg atccaccaca cacccacct gtgcttcgtg     1440 cacaccgtgc cctgggacca gctgttccgc aaccccacc aggccctgct gcacaccgcc     1500
aaccgccccg aggacgagtg cgtgggcgag ggcctggcct gccaccagct gtgcgcccgc     1560
ggccactgct ggggcccccgg ccccacccag tgcgtgaact gcagccagtt cctgcgcggc     1620
caggagtgcg tggaggagtg ccgcgtgctg cagggcctgc cccgcgagta cgtgaacgcc     1680
cgccactgcc tgccctgcca ccccgagtgc cagccccaga cggcagcgt gacctgcttc     1740 ggccccgagg ccgaccagtg cgtggcctgc gcccactaca aggaccccc cttctgcgtg     1800 gcccgctgcc ccagcggcgt gaagcccgac ctgagctaca tgcccatctg gaagttcccc     1860
gacgaggagg gcgcctgcca gccctgcccc atcaactgca cccacagctg cgtggacctg     1920
gacgacaagg gctgccccgc cgagcagcgc gccagccccc tgaccagcat catcagcgcc     1980
gtggtgggca tcctgctggt ggtggtgctg ggcgtggtgt tcggcatcct gatcaagcgc     2040
cgccagcaga gatccgcaa gtacaccatg cgccgcctgc tgcaggagac cgagctggtg     2100
gagcccctga cccccagcgg cgccatgccc aaccaggccc agatgcgcat cctgaaggag     2160
accgagctgc gcaaggtgaa ggtgctgggc agcggcgcct tcggcaccgt gtacaagggc     2220
atctggatcc ccgacggcga gaacgtgaag atccccgtgg ccatcgccgt gctgcgcgag     2280
aacaccagcc ccaaggccaa caaggagatc ctggacgagg cctacgtgat ggccggcgtg     2340 ggcagccccct acgtgagccg cctgctgggc atctgcctga ccagcaccgt gcagctggtg     2400
acccagctga tgcctacgg ctgcctgctg gaccacgtgc gcgagaaccg cggccgcctg     2460
```

```
ggcagccagg acctgctgaa ctggtgcatg cagatcgcca agggcatgag ctacctggag    2520
gacgtgcgcc tggtgcaccg cgacctggcc gcccgcaacg tgctggtgaa gagccccaac    2580
cacgtgaaga tcaccgactt cggcctggcc cgcctgctgg acatcgacga gaccgagtac    2640
cacgccgacg gcggcaaggt gcccatcaag tggatggccc tggagagcat cctgcgccgc    2700
cgcttcaccc accagagcga cgtgtggagc tacggcgtga ccgtgtggga gctgatgacc    2760
ttcggcgcca agccctacga cggcatcccc gcccgcgaga tccccgacct gctggagaag    2820
ggcgagcgcc tgccccagcc ccccatctgc accatcgacg tgtacatgat catggtgaag    2880
tgctggatga tcgacagcga gtgccgcccc cgcttccgcg agctggtgag cgagttcagc    2940
cgcatggccc gcgacccca cgcttcgtg gtgatccaga cgaggacct gggcccgcc    3000 agcccctgg acagcacctt ctaccgcagc ctgctggagg acgacgacat gggcgacctg    3060
gtggacgccg aggagtacct ggtgccccag cagggcttct tctgccccga ccccgccccc    3120
ggcgccggcg gcatggtgca ccaccgccac cgcagcagca gcacccgcag cggcggcggc    3180
gacctgaccc tgggcctgga gcccagcgag gaggaggccc ccgcagccc cctggccccc    3240 agcgagggcg ccggcagcga cgtgttcgac ggcgacctgg gcatgggcgc cgccaagggc    3300
ctgcagagcc tgccccaccca cgaccccagc ccctgcagc gctacagcga ggaccccacc    3360
gtgcccctgc ccagcgagac cgacggctac gtggccccc tgacctgcag ccccagccc    3420 gagtacgtga accagcccga cgtgcgcccc cagccccca gccccgcga gggcccctg    3480 cccgccgccc gccccgccgg cgccaccctg gagcgcccca gaccctgag ccccggcaag    3540 aacggcgtgg tgaaggacgt gttcgccttc ggcggcgccg tggagaaccc cgagtacctg    3600
accccccagg gcgagctgc tcctcagcct caccctccac ctgctttcag ccctgctttc    3660
gacaacctgt actactggga ccaggaccct cctgagaggg gtgctcctcc tagcaccttc    3720
aagggcaccc ccaccgccga gaaccccgag tacctgggcc tggacgtgcc cgtgtaaa     3778

<210> SEQ ID NO 12
<211> LENGTH: 33
<212> TYPE: DNA
<213> ORGANISM: Artificial Sequence
<220> FEATURE:
<223> OTHER INFORMATION: PCR Primer

<400> SEQUENCE: 12
ccagatatcg aattctagag ccgccaccat gga                                 33

<210> SEQ ID NO 13
<211> LENGTH: 41
<212> TYPE: DNA
<213> ORGANISM: Artificial Sequence
<220> FEATURE:
<223> OTHER INFORMATION: PCR Primer

<400> SEQUENCE: 13
gctgtcgact ttatcagatc aggatgccga acaccacgcc c                        41

<210> SEQ ID NO 14
<211> LENGTH: 675
<212> TYPE: PRT
<213> ORGANISM: Artificial Sequence
<220> FEATURE:
<223> OTHER INFORMATION: HER2ECDTM polypeptide

<400> SEQUENCE: 14
```

-continued

```
Met Glu Leu Ala Ala Leu Cys Arg Trp Gly Leu Leu Leu Ala Leu Leu
 1               5                  10                  15

Pro Pro Gly Ala Ala Ser Thr Gln Val Cys Thr Gly Thr Asp Met Lys
             20                  25                  30

Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
 50                  55                  60

Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
             100                 105                 110

Ala Leu Ala Val Leu Asp Asn Gly Asp Pro Leu Asn Asn Thr Thr Pro
         115                 120                 125

Val Thr Gly Ala Ser Pro Gly Gly Leu Arg Glu Leu Gln Leu Arg Ser
 130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                 165                 170                 175

Asn Gln Leu Ala Leu Thr Leu Ile Asp Thr Asn Arg Ser Arg Ala Cys
             180                 185                 190

His Pro Cys Ser Pro Met Cys Lys Gly Ser Arg Cys Trp Gly Glu Ser
         195                 200                 205

Ser Glu Asp Cys Gln Ser Leu Thr Arg Thr Val Cys Ala Gly Gly Cys
 210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                 245                 250                 255

His Phe Asn His Ser Gly Ile Cys Glu Leu His Cys Pro Ala Leu Val
             260                 265                 270

Thr Tyr Asn Thr Asp Thr Phe Glu Ser Met Pro Asn Pro Glu Gly Arg
         275                 280                 285

Tyr Thr Phe Gly Ala Ser Cys Val Thr Ala Cys Pro Tyr Asn Tyr Leu
 290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                 325                 330                 335

Pro Cys Ala Arg Val Cys Tyr Gly Leu Gly Met Glu His Leu Arg Glu
             340                 345                 350

Val Arg Ala Val Thr Ser Ala Asn Ile Gln Glu Phe Ala Gly Cys Lys
         355                 360                 365

Lys Ile Phe Gly Ser Leu Ala Phe Leu Pro Glu Ser Phe Asp Gly Asp
 370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                 405                 410                 415

Asp Ser Leu Pro Asp Leu Ser Val Phe Gln Asn Leu Gln Val Ile Arg
```

-continued

```
                420             425             430
Gly Arg Ile Leu His Asn Gly Ala Tyr Ser Leu Thr Leu Gln Gly Leu
            435             440             445
Gly Ile Ser Trp Leu Gly Leu Arg Ser Leu Arg Glu Leu Gly Ser Gly
450             455             460
Leu Ala Leu Ile His His Asn Thr His Leu Cys Phe Val His Thr Val
465             470             475             480
Pro Trp Asp Gln Leu Phe Arg Asn Pro His Gln Ala Leu Leu His Thr
            485             490             495
Ala Asn Arg Pro Glu Asp Glu Cys Val Gly Glu Gly Leu Ala Cys His
            500             505             510
Gln Leu Cys Ala Arg Gly His Cys Trp Gly Pro Gly Pro Thr Gln Cys
            515             520             525
Val Asn Cys Ser Gln Phe Leu Arg Gly Gln Glu Cys Val Glu Glu Cys
530             535             540
Arg Val Leu Gln Gly Leu Pro Arg Glu Tyr Val Asn Ala Arg His Cys
545             550             555             560
Leu Pro Cys His Pro Glu Cys Gln Pro Gln Asn Gly Ser Val Thr Cys
            565             570             575
Phe Gly Pro Glu Ala Asp Gln Cys Val Ala Cys Ala His Tyr Lys Asp
            580             585             590
Pro Pro Phe Cys Val Ala Arg Cys Pro Ser Gly Val Lys Pro Asp Leu
            595             600             605
Ser Tyr Met Pro Ile Trp Lys Phe Pro Asp Glu Glu Gly Ala Cys Gln
            610             615             620
Pro Cys Pro Ile Asn Cys Thr His Ser Cys Val Asp Leu Asp Asp Lys
625             630             635             640
Gly Cys Pro Ala Glu Gln Arg Ala Ser Pro Leu Thr Ser Ile Ile Ser
            645             650             655
Ala Val Val Gly Ile Leu Leu Val Val Val Leu Gly Val Val Phe Gly
            660             665             670
Ile Leu Ile
            675
```

SYNTHETIC GENE ENCODING HUMAN EPIDERMAL GROWTH FACTOR 2/NEU ANTIGEN AND USES THEREOF

CROSS-REFERENCE TO RELATED APPLICATIONS

This application is a continuation of U.S. Ser. No. 10/565,418, filed Jan. 23, 2006 now abandoned, which is a §371 National Stage Application of PCT/EP2004/008234, international filing date of Jul. 20, 2004, which claims the benefit of U.S. Provisional Application No. 60/489,237 filed Jul. 21, 2003, now expired.

FIELD OF THE INVENTION

The present invention relates generally to the therapy of cancer. More specifically, the present invention relates to synthetic polynucleotides encoding the human tumor associated polypeptide epidermal growth factor 2/neu antigen, herein designated hHER2.opt, wherein the polynucleotides are codon-optimized for expression in a human cellular environment. The present invention also relates to synthetic polynucleotides encoding a truncated form of the HER2/neu antigen, herein designated hHER2ECDTM.opt, wherein the polynucleotides are codon-optimized for expression in a human cellular environment. The present invention further relates to recombinant vectors and hosts comprising said synthetic polynucleotides. This invention also provides adenoviral vector and plasmid constructs carrying hHER2.opt and to their use in vaccines and pharmaceutical compositions for preventing and treating cancer.

BACKGROUND OF THE INVENTION

Epidermal growth factor 2 is a transmembrane tumor associated antigen encoded by the HER2/neu proto-oncogene (also called c-erbB-2), which is a member of the epidermal growth factor receptor family of cell surface receptors. The HER2 gene was originally isolated from a rat neuroglioblastoma (Shih et al., *Nature* 290: 261-264 (1981)) and later cloned and characterized from human cells (Coussens et al., *Science* 230: 1132-39 (1985); King et al., *Science* 229: 974-76 (1985)).

HER2/neu is further classified as a member of the HER family of receptor tyrosine kinases, which consists of four receptors that participate in cell growth and differentiation. The HER receptors contribute to maintaining normal cell growth by binding growth factor ligands as dimers. Specifically, human HER2 forms heterodimers with other members of the EGFR family (HER1, HER3 and HER4) (Klapper et al. *Adv Cancer Res* 77: 25-79 (2000)). Following hHER2 dimerization and tyrosine auto-phosphorylation, docking sites for cytoplasmic signaling molecules are generated and recruitment of second signaling molecules is initiated. Intracellular signaling cascades, which ultimately result in the activation of genes important in cell growth, are thus initiated.

Low levels of expression of the HER2/neu transcript and the encoded 185 kD protein are normally detected in adult epithelial cells of various tissues, including the skin and breast, and tissues of the gastrointestinal, reproductive and urinary tracts (Press et al., *Oncogene* 5: 953-962 (1990)). Higher levels of HER2/neu expression are also detected in the corresponding fetal tissues during embryonic development (Press et al., supra).

Several observations make the HER2 antigen an attractive target for active specific immunotherapy. First, the HER/neu gene is commonly overexpressed or amplified in various malignancies, such as carcinomas of the breast, ovary, uterus, colon, and prostate, and adenocarcinomas of the lung (reviewed in Disis and Cheever, *Adv. Cancer Research* 71: 343-371 (1997)). Overexpression of HER2/neu correlates with a poor prognosis and a higher relapse rate for cancer patients (Slamon et al., *Science* 244: 707-712 (1989)). Amplification of human HER2 leads to enhanced MAP kinase activity and cell proliferation, and contributes to the aggressive behavior of tumor cells (Ben-Levy et al. *Embo J* 13(14): 3302-11 (1994)). The high expression level of HER2 observed in tumors is in direct contrast with the low levels associated with normal adult tissues.

Additionally, many cancer patients suffering from malignancies associated with HER2/neu overexpression have had immune responses against the HER2 protein. Anti-hHER2 cytotoxic T lymphocytes (CTL) have been isolated from breast and ovarian cancer patients (Ioannides et al. *Cell Immunol* 151(1): 225-34 (1993); Peoples et al. *Proc Natl Acad Sci USA* 92 (14): 6547-51 (1995)). Several HLA-A2.1-associated hHER2 peptides have been defined and peptide-specific T cells can be generated in vitro (Fisk et al. *Cancer Res* 57(1): 8-93 (1997); Yoshino et al. *Cancer Res* 54(13): 3387-90 (1994); Lustgarten et al. *Hum Immunol* 52(2): 109-18 (1997)).

The above findings demonstrate that anti-ErbB-2 immune effector mechanisms are activated in cancer patients and highlight the potential benefit of enhancing such immune reactivity. An effective vaccine exploiting the immune response to HER2/neu must both enhance this immunity to a level that is protective and/or preventive and overcome self-tolerance.

Based on the above recitation, HER2/neu has been pursued as a target for the development of immunological treatments of malignancies. Anti-HER2 monoclonal antibodies have been investigated as therapies for breast cancer, with each antibody approach demonstrating various levels of success (for discussion, see Yarden, *Oncology* 61 (suppl 2): 1-13 (2001)).

Additionally, DNA and peptide-based vaccines targeting HER2/neu have been reported. Amici et al. (U.S. Pat. No. 6,127,344) disclose a method for inducing immunity against HER2/neu by administering an expression vector comprising the full-length human HER2/neu cDNA functionally linked to the human cytomegalovirus promoter. Morris et al. (WO 2004/041065) disclose a method of vaccination with dendritic cells modified by adenoviral vectors expressing a non-signaling HER2/neu gene. Cheever and Disis disclose methods for immunizing humans against HER2/neu-associated cancers with HER2 peptides (U.S. Pat. No. 5,846,538). Additionally, HER2/neu peptide-based vaccines have been studied in rodent models (for review, see Disis and Cheever, *Adv. Cancer Res.* 71:343-71 (1997)).

The development and commercialization of many vaccines have been hindered by difficulties associated with obtaining high expression levels of exogenous genes in successfully transformed host organisms. Therefore, despite the identification of the wild-type nucleotide sequences encoding hHER2 protein described above, it would be highly desirable to develop a readily renewable source of human HER2 protein that utilizes hHER2-encoding nucleotide sequences that are optimized for expression in the intended host cell, said source allowing for the development of a cancer vaccine which is efficacious and not hindered by self-tolerance.

SUMMARY OF THE INVENTION

The present invention relates to compositions and methods to elicit or enhance immunity to the protein products expressed by the human HER2 gene, which is associated with numerous adenocarcinomas, including breast and ovarian cancers. Specifically, the present invention provides polynucleotides encoding human HER2 protein, or a truncated form of human HER2 protein which comprises the extracellular and transmembrane domains of the HER2 protein (hereinafter hHER2ECDTM), wherein said polynucleotides are codon-optimized for high level expression in a human cell. The present invention further provides adenoviral and plasmid-based vectors comprising the synthetic polynucleotides and discloses use of said vectors in immunogenic compositions and vaccines for the prevention and/or treatment of HER2-associated cancer. The polynucleotides described herein are more efficient that wild-type HER2 in eliciting a cellular and humoral immune response against human HER2.

The present invention also relates to synthetic nucleic acid molecules (polynucleotides) comprising a sequence of nucleotides that encode human epidermal growth factor 2 antigen (hereinafter hHER2) as set forth in SEQ ID NO:2, wherein the synthetic nucleic acid molecules are codon-optimized for high-level expression in a human cell (hereinafter hHER2.opt). The present invention further relates to synthetic nucleic acid molecules (polynucleotides) comprising a sequence of nucleotides that encode human HER2ECDTM as set forth in SEQ ID NO:14, wherein the synthetic nucleic acid molecules are codon-optimized for high-level expression in a human cell. The nucleic acid molecules disclosed herein may be transfected into a host cell of choice wherein the recombinant host cell provides a source for substantial levels of an expressed functional hHER2 protein (SEQ ID NO:2) or hHER2ECDTM protein (SEQ ID NO:14).

The present invention further relates to a synthetic nucleic acid molecule which encodes mRNA that expresses a human HER2 protein. A preferred aspect of this portion of the present invention is disclosed in FIG. 1, which shows a DNA molecule (SEQ ID NO:1) that encodes a hHER2 protein (SEQ ID NO:2). The preferred nucleic acid molecule of the present invention is codon-optimized for high-level expression in a human cell. The sequence of this preferred polynucleotide also contains a mutation abolishing tyrosine kinase activity (AAA2257GCC, K753A). Nucleotide sequences that do not contain this mutation are also contemplated by this invention.

The present invention additionally relates to a synthetic nucleic acid molecule which encodes mRNA that expresses a human HER2ECDTM protein. A preferred aspect of this portion of the present invention is disclosed in FIG. 6A, which shows a DNA molecule (SEQ ID NO:9) that encodes a hHER2ECDTM protein (SEQ ID NO:14). The preferred nucleic acid molecule of the present invention is codon-optimized for high-level expression in a human cell.

The present invention also relates to recombinant vectors and recombinant host cells, both prokaryotic and eukaryotic, which contain the nucleic acid molecules disclosed throughout this specification.

The present invention further relates to a process for expressing a codon-optimized human HER2 protein in a recombinant host cell, comprising: (a) introducing a vector comprising a synthetic polynucleotide encoding a human HER2 protein into a suitable host cell, wherein the synthetic polynucleotide is codon-optimized for optimal expression in a human cell; and, (b) culturing the host cell under conditions which allow expression of said human HER2 protein.

The present invention also relates to a process for expressing a codon-optimized human HER2ECDTM protein in a recombinant host cell, comprising: (a) introducing a vector comprising a synthetic polynucleotide encoding a human HER2ECDTM protein into a suitable host cell, wherein the synthetic polynucleotide is codon-optimized for optimal expression in a human cell; and, (b) culturing the host cell under conditions which allow expression of said human HER2ECDTM protein.

Another aspect of this invention is a method of preventing or treating cancer comprising administering to a mammal a vaccine vector comprising a synthetic nucleic acid molecule, the synthetic nucleic acid molecule comprising a sequence of nucleotides that encodes a human epidermal growth factor 2 antigen (hHER2) protein as set forth in SEQ ID NO:2, or a human HER2ECDTM protein as set forth in SEQ ID NO:14, wherein the synthetic nucleic acid molecule is codon-optimized for high level expression in a human cell.

The present invention further relates to an adenovirus vaccine vector comprising an adenoviral genome with a deletion in the E1 region, and an insert in the E1 region, wherein the insert comprises an expression cassette comprising: (a) a codon-optimized polynucleotide encoding a human HER2 protein or a human HER2ECDTM protein; and (b) a promoter operably linked to the polynucleotide.

The present invention also relates to a vaccine plasmid comprising a plasmid portion and an expression cassette portion, the expression cassette portion comprising: (a) a synthetic polynucleotide encoding a human HER2 protein or a human HER2ECDTM protein, wherein the synthetic polynucleotide is codon-optimized for optimal expression in a human cell; and (b) a promoter operably linked to the polynucleotide.

Another aspect of the present invention is a method of protecting a mammal from cancer or treating a mammal suffering from HER2-associated cancer comprising: (a) introducing into the mammal a first vector comprising: i) a codon-optimized polynucleotide encoding a human HER2 protein or a human HER2ECDTM protein; and ii) a promoter operably linked to the polynucleotide; (b) allowing a predetermined amount of time to pass; and (c) introducing into the mammal a second vector comprising: i) a codon-optimized polynucleotide encoding a human HER2 protein or a human HER2ECDTM protein; and ii) a promoter operably linked to the polynucleotide.

As used throughout the specification and in the appended claims, the singular forms "a," "an," and "the" include the plural reference unless the context clearly dictates otherwise.

As used throughout the specification and appended claims, the following definitions and abbreviations apply:

The term "promoter" refers to a recognition site on a DNA strand to which the RNA polymerase binds. The promoter forms an initiation complex with RNA polymerase to initiate and drive transcriptional activity. The complex can be modified by activating sequences termed "enhancers" or inhibiting sequences termed "silencers".

The term "cassette" refers to a nucleotide or gene sequence that is to be expressed from a vector, for example, the nucleotide or gene sequence encoding the HER2 protein or the HER2ECDTM protein. In general, a cassette comprises a gene sequence inserted into a vector which, in some embodiments, provides regulatory sequences for expressing the nucleotide or gene sequence. In other embodiments, the nucleotide or gene sequence provides the regulatory sequences for its expression. In further embodiments, the vector provides some regulatory sequences and the nucleotide or gene sequence provides other regulatory sequences. For example, the vector can provide a promoter for transcribing the nucleotide or gene sequence and the nucleotide or gene sequence provides a transcription termination sequence. The regulatory sequences which can be provided by the vector include, but are not limited to, enhancers, transcription termination sequences, splice acceptor and donor sequences, introns, ribosome binding sequences, and poly(A) addition sequences. The cassette is similar in concept to a cassette tape; each cassette has its own sequence. Thus by interchanging the cassette, the vector will express a different sequence. Because of the restriction sites at the 5' and 3' ends, the cassette can be easily inserted, removed or replaced with another cassette.

The term "vector" refers to some means by which DNA fragments can be introduced into a host organism or host tissue. There are various types of vectors including plasmid, virus (including adenovirus), bacteriophages and cosmids.

The term "first generation," as used in reference to adenoviral vectors, describes said adenoviral vectors that are replication-defective. First generation adenovirus vectors typically have a deleted or inactivated E1 gene region, and preferably have a deleted or inactivated E3 gene region.

The designation "pV1J-hHER2.opt" refers to a plasmid construct, disclosed herein, comprising the human CMV immediate-early (IE) promoter with intron A, a full-length codon-optimized human HER2 gene, bovine growth hormone-derived polyadenylation and transcriptional termination sequences, and a minimal pUC backbone (see EXAMPLE 2).

The designation "pV1J-hHER2ECDTM.opt" refers to a plasmid construct, disclosed herein, comprising the human CMV immediate-early (IE) promoter with intron A, a truncated codon-optimized human HER2 gene comprising the extracellular and transmembrane domains of the HER2 gene, bovine growth hormone-derived polyadenylation and transcriptional termination sequences, and a minimal pUC backbone (see EXAMPLE 2).

The designation "pV1J-hHER2.wt" refers to a construct as described above, except the construct comprises a wild-type full-length human HER2 gene instead of a codon-optimized human HER2 gene.

The designation "pV1J-hHER2ECDTM.wt" refers to a construct as described above, except the construct comprises a wild-type truncated human HER2 gene, said truncated gene comprising a sequence of nucleotides that encode the extracellular and transmembrane domains of the HER2 protein, instead of a codon-optimized full-length human HER2 gene.

The designations "MRKAd5-hHER2.opt," "MRKAd5-hHER2ECDTM.opt" and "MRKAd5-hHER2.wt" refer to three constructs, disclosed herein, which comprise an Ad5 adenoviral genome deleted of the E1 and E3 regions. In the "MRKAd5-hHER2.opt" construct, the E1 region is replaced by a codon-optimized full-length human HER2 gene in an E1 parallel orientation under the control of a human CMV promoter without intron A, followed by a bovine growth hormone polyadenylation signal. The "MRKAd5-hHER2ECDTM.opt" construct is essentially as described above, except the E1 region of the Ad5 genome is replaced by a codon-optimized truncated version of the human HER2 gene, said truncated HER2 gene comprising a sequence of nucleotides that encode the extracellular and the transmembrane domains of the HER2 receptor. The "MRKAd5-hHER2.wt" construct is essentially as described above, except the E1 region of the Ad5 genome is replaced with a wild-type full-length human HER2 sequence (see EXAMPLE 11).

The term "effective amount" means sufficient vaccine composition is introduced to produce the adequate levels of the polypeptide, so that an immune response results. One skilled in the art recognizes that this level may vary.

The term "treatment" refers to both therapeutic treatment and prophylactic or preventative measures. Those in need of treatment include those already with the disorder as well as those prone to have the disorder or those in which the disorder is to be prevented.

A "disorder" is any condition that would benefit from treatment with the methods or the vaccines and immunogenic compositions described herein. This term includes chronic and acute disorders or diseases including those pathological conditions which predispose the mammal to the disorder in question. The methods and the vaccines of the present invention are intended for the treatment of disorders or conditions associated with aberrant HER2/neu-associated expression or signaling, including, but in no way limited to, breast, colorectal, gastric, ovarian, and lung cancer.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid).

"hHER2.wt" and "hHER2.opt" refer to a human epidermal growth factor 2 antigen and a human codon-optimized epidermal growth factor 2 antigen, respectively.

"hHER2ECDTM.wt" and "hHER2ECDTM.opt" refer to a truncated human epidermal growth factor 2 antigen and a truncated human codon-optimized epidermal growth factor 2 antigen, respectively. The truncated forms of HER2, "hHER2ECDTM.wt" and "hHER2ECDTM.opt," comprise the extracellular and transmembrane domains of the human HER2 protein.

The term "mammalian" refers to any mammal, including a human being.

The abbreviation "Ag" refers to an antigen.

The abbreviations "Ab" and "mAb" refer to an antibody and a monoclonal antibody, respectively.

The abbreviation "ORF" refers to the open reading frame of a gene.

BRIEF DESCRIPTION OF THE DRAWINGS

FIG. 1 and FIG. 1A-1 shows the nucleotide sequence of a codon-optimized polynucleotide (hHER2.opt, SEQ ID NO:1) that encodes human HER2 protein. See EXAMPLE 1. Panel B shows the deduced amino acid sequence of the human HER2 protein (SEQ ID NO:2).

FIG. 2 shows the identification of immunodominant T-cell epitopes in the human HER2 protein by ELISPOT and intracellular staining (ICS) analysis. BALB/c mice immunized with Ad5-hHER2 were analyzed for the induction of human HER2-specific cellular immunity. The number of IFN-γ-secreting anti-human HER2 T cells was determined by ELISPOT on splenocytes from groups of mice (indicated in the first column) using pools or single peptides. Data displayed are representative of several independent experiments. Values are expressed as the number of spot forming colonies (SFC)/$10^6$ total splenocytes, subtracted of the background values determined in the absence of peptides (typically less than 10 SFC/10⁶ total splenocytes). Numbers corresponding to more than three times the background measured in control experiments without antigenic peptides were considered positive values and are indicated in boldface. Frequency of CD4⁺ or CD8⁺ T-cell secreting IFN-γ was measured by ICS. Data displayed are representative of several independent experiments. Values are expressed as 1000×[(IFN-γ CD3⁺ and CD4⁺ or CD8⁺)/(CD3⁺ and CD4⁺ or CD8⁺)]. Values higher than 1% were considered positive and indicated in boldface. Sequences encompassed by the pool or by the single peptide used in the assay are indicated on the left. Numbers refers to the position of amino acid residue of the human HER2 protein.

FIG. 4 shows the immune response to human HER2 in BALB/c mice. Panel (A) shows that codon-optimized HER2 yielded significantly improved ELISPOT values compared to wild type HER2. Shown are results from immunization of four groups, each comprising two mice, with plasmid pV1J-hHER2.wt or pV1J-hHER2.opt (50 μg/dose electroinjected in the quadriceps muscle). Two weeks after the last injection, the frequency of IFN-γ secreting T cells in mouse splenocytes was determined via IFN-γ ELISPOT assay using peptides hNeu15.3 (aa 63-71, including a CD8+ epitope), hNeu301 (aa 1202-1214, including a CD8+ epitope) and hNeu42 (aa 165-179, including a CD4+ epitope). Results from $2.5 \times 10^5$ and $5 \times 10^5$ splenocytes, with two replicas of each amount tested, are shown. Average values were calculated by subtracting the background level determined in the absence of peptides (typically less than 10 SFC/10⁶ total splenocytes). Results were expressed as the number of SFC/10⁶ total splenocytes. Panel (B) shows that pV1J-hHER2.opt elicits a significantly improved IgG1 and IgG2a humoral response compared to pV1J-hHER2.wt. Serum samples were collected at week 6 (the day before the first immunization, pre-bleed) and week 14 (two weeks after the last injection) from groups of 4 mice immunized with pV1J-hHER2.wt or pV1J-hHER2.opt plasmid DNA. Anti-hHER2 antibody titers in the pooled sera from each group of mice were measured by ELISA using the dimeric extra-cellular domain of hHER2 (HER2-ECD) as target antigen. AP-conjugated goat anti-mouse IgG1 or IgG2a was used to detect bound mouse antibodies.

FIG. 5 shows a comparison of p185-specific T-cell response elicited in mice by immunization with pV1J-HER2 and Ad5-HER2. Wild-type BALB/c mice and BALB/c transgenic mice overexpressing rat HER2 (indicated as NeuT, see Lucchini et al., Cancer Lett 64(3): 203-9 (1992)) were immunized at 6 and 9 weeks of age, either with pV1J-hHER2.wt DNA (50 μg/dose, injected in the quadriceps muscle), followed by electrical stimulation or with Ad5-hHER2.wt. At 12 weeks of age, the number of IFN-γ-secreting anti-human cells was determined by ELISPOT analysis from pools of mice using the peptides indicated. Data displayed are representative of several independent experiments. Values are expressed as in FIG. 1.

FIG. 6, panel A, shows the nucleotide sequence of a codon-optimized polynucleotide (hHER2ECDTM.opt, SEQ ID NO:9) that encodes a truncated human HER2 protein, said protein comprising the extracellular and transmembrane domains of the HER2 protein. Panel B shows a second polynucleotide that encodes the extracellular and transmembrane domains of the HER2 protein, the second polynucleotide comprising "wild-type" nucleotide sequences, which have not been codon optimized (hHER2ECDTM.wt, SEQ ID NO:10).

FIG. 7 shows an analysis of the cell-mediated response induced in rhesus monkeys immunized with a mixture of three plasmids expressing human antigens HER2, CEA and EpCAM, said plasmids comprising nucleotide sequences that are codon-optimized for high-level expression in human cells. The same animals were then immunized with a mixture of three Ad5 vectors expressing the wild-type sequence of each of the three antigens. Cell-mediated immune response directed against the highly homologous (98.2% sequence similarity) rhesus monkey HER2 protein was measured by IFN-γ ELISPOT every month for one year. Values are expressed as SFC/10⁶ PBMC, subtracted of the background values determined in the absence of peptides. Values which are significantly different (p<0.05) from background, as measured in control experiments without antigenic peptides, and higher than the arbitrarily chosen threshold of 55 SFC/10⁶ PBMC are indicated in boldface.

FIG. 8 shows a comparison of the cell-mediated immune response elicited in mice by immunization with pV1J-hHER2opt and pV1J-hHER2ECDTM.opt. Values refer to the frequency of IFNγ-secreting spleen cells as measured by ELISPOT. Data displayed are derived from three animals and are representative of several independent experiments. Values are expressed as SFC/10⁶ total spleen cells, subtracted of the background values determined in the absence of peptides (typically less than 5 SFC/10⁶ spleen cells). Values which are significantly different (p<0.05) from background, as measured in control experiments without antigenic peptides, and are higher than the arbitrarily chosen threshold of 25 SFC/10⁶ spleen cells are indicated in boldface.

DETAILED DESCRIPTION OF THE INVENTION

Figure 3A:
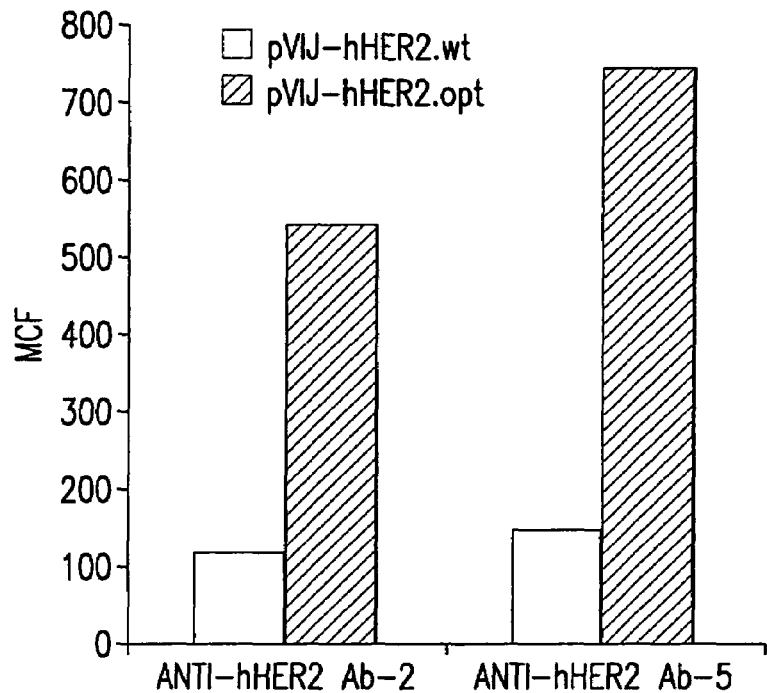
FIG. 3 shows the in vitro expression of hHER2 following transfection in (A) human embryonic kidney HEK-293 cells and (B) mouse myoblasts C2C7. Data are expressed as the geometric mean of the channel fluorescence from which the signal generated by the empty pV1JnsA plasmid has been subtracted. For C2C7 cells, data are normalized on the efficiency of pEGFP DNA transfection.

Human epidermal growth factor 2 (hHER2) is commonly associated with a number of different types of tumors, including breast, ovarian, gastric, and colon carcinomas. The present invention relates to compositions and methods to elicit or enhance immunity to the protein product expressed by the hHER2 gene, wherein aberrant hHER2 expression is associated with the carcinoma or its development. Association of aberrant hHER2 expression with a carcinoma does not require that the hHER2 protein be expressed in tumor tissue at all time points of its development, as abnormal hHER2 expression may be present at tumor initiation and not be detectable late into tumor progression or vice-versa.

To this end, synthetic DNA molecules encoding a full-length human HER2 protein or a truncated human HER2 protein, referred to herein as HER2ECDTM, are provided. Said truncated HER2 comprises the extracellular and transmembrane domains of the human HER2 protein. The codons of the synthetic DNA molecules are designed so as to use the codons preferred by the projected host cell, which in preferred embodiments is a human cell. The synthetic molecules may be used for the development of plasmid-based vaccines or recombinant adenovirus, which provide effective immunoprophylaxis against HER2-associated cancer through neutralizing antibody and cell-mediated immunity. The synthetic molecules may be used as an immunogenic composition. This invention provides polynucleotides which, when directly introduced into a vertebrate in vivo, including mammals such as primates and humans, induce the expression of encoded proteins within the animal.

The wild-type human HER2 nucleotide sequence has been reported (Coussens et al., *Science* 230: 1132-39 (1985); King et al., *Science* 229: 974-76 (1985)). The present invention provides synthetic DNA molecules encoding the full-length human HER2 protein, or a truncated human HER2 protein, HER2ECDTM, comprising the extracellular and transmembrane domains of hHER2. The synthetic molecules of the present invention comprise a sequence of nucleotides, wherein at least one of the nucleotides has been altered so as to use the codons preferred by a human cell, thus allowing for high-level expression of hHER2 or hHER2ECDTM in a human host cell. The synthetic molecules may be used as a source of hHER2 or hHER2ECDTM protein, which may be used in a cancer vaccine to provide effective immunoprophylaxis against hHER2-associated carcinomas through neutralizing antibody and cell-mediated immunity. Alternatively, the synthetic molecules may be used as the basis of a DNA vaccine or adenovirus vaccine.

A "triplet" codon of four possible nucleotide bases can exist in over 60 variant forms. Because these codons provide the message for only 20 different amino acids (as well as transcription initiation and termination), some amino acids can be coded for by more than one codon—a phenomenon known as codon redundancy. For reasons not completely understood, alternative codons are not uniformly present in the endogenous DNA of differing types of cells. Indeed, there appears to exist a variable natural hierarchy or "preference" for certain codons in specific types of cells. As one example, the amino acid leucine is specified by any of six DNA codons including CTA, CTC, CTG, CTT, TTA, and TTG. Exhaustive analysis of genome codon frequencies for microorganisms has revealed endogenous DNA of *E. coli* most commonly contains the CTG leucine-specifying codon, while the DNA of yeasts and slime molds most commonly includes a TTA leucine-specifying codon. In view of this hierarchy, it is generally believed that the likelihood of obtaining high levels of expression of a leucine-rich polypeptide by an *E. coli* host will depend to some extent on the frequency of codon use. For example, it is likely that a gene rich in TTA codons will be poorly expressed in *E. coli*, whereas a CTG rich gene will probably be highly expressed in this host. Similarly, a preferred codon for expression of a leucine-rich polypeptide in yeast host cells would be TTA.

The implications of codon preference phenomena on recombinant DNA techniques are manifest, and the phenomenon may serve to explain many prior failures to achieve high expression levels of exogenous genes in successfully transformed host organisms—a less "preferred" codon may be repeatedly present in the inserted gene and the host cell machinery for expression may not operate as efficiently. This phenomenon suggests that synthetic genes which have been designed to include a projected host cell's preferred codons provide an optimal form of foreign genetic material for practice of recombinant DNA techniques. Thus, one aspect of this invention is a human HER2 gene that is codon-optimized for high-level expression in a human cell. In a preferred embodiment of this invention, it has been found that the use of alternative codons encoding the same protein sequence may remove the constraints on expression of exogenous hHER2 protein in human cells. Another aspect of this invention is a truncated human HER2 gene, hHER2ECDTM, that is codon optimized for high-level expression in a human host cell, said truncated HER2 gene comprising nucleotide sequences that encode the extracellular and transmembrane domains of human HER2.

In accordance with this invention, the human HER2 gene sequence and the human HER2ECDTM gene sequence were converted to polynucleotide sequences having identical translated sequences as compared to wild-type equivalents, but with alternative codon usage as described by Lathe, "Synthetic Oligonucleotide Probes Deduced from Amino Acid Sequence Data: Theoretical and Practical Considerations" *J. Molec. Biol.* 183:1-12 (1985), which is hereby incorporated by reference. The methodology generally consists of identifying codons in the wild-type sequence that are not commonly associated with highly expressed human genes and replacing them with optimal codons for high expression in human cells. Said optimal codons are referred to herein as "human-preferred" codons. The new gene sequence is then inspected for undesired sequences generated by codon replacements (e.g., "ATTTA" sequences, inadvertent creation of intron splice recognition sites, unwanted restriction enzyme sites, high GC content, etc.). Undesirable sequences are eliminated by substitution of the existing codons with different codons coding for the same amino acid. The synthetic gene segments are then tested for improved expression.

The methods described above were used to create synthetic gene sequences for human HER2 and human HER2ECDTM, resulting in full-length and truncated genes comprising codons optimized for high level expression in human cells. While the above procedure provides a summary of our methodology for designing codon-optimized genes for use in cancer vaccines, it is understood by one skilled in the art that similar vaccine efficacy or increased expression of genes may be achieved by minor variations in the procedure or by minor variations in the sequence. One of skill in the art will also recognize that additional DNA molecules may be constructed that provide for high levels of hHER2 or hHER2ECDTM expression in human cells, wherein only a portion of the codons of the DNA molecules are codon-optimized. The nucleic acid molecules of the present invention are substantially free from other nucleic acids.

Accordingly, the present invention relates to a synthetic polynucleotide comprising a sequence of nucleotides encoding a human HER2 protein, for example, the human HER2 protein set forth in SEQ ID NO:2, or a biologically active fragment or mutant form of a human HER2 protein, the polynucleotide sequence comprising codons optimized for expression in a human host. Said mutant forms of the hHER2 protein include, but are not limited to: conservative amino acid substitutions, amino-terminal truncations, carboxy-terminal truncations, deletions, or additions. Any such biologically active fragment and/or mutant will encode either a protein or protein fragment which at least substantially mimics the immunological properties of the hHER2 protein as set forth in SEQ ID NO:2. The synthetic polynucleotides of the present invention encode mRNA molecules that express a functional human HER2 protein so as to be useful in the development of a therapeutic or prophylactic cancer vaccine.

A preferred polynucleotide of the present invention is a polynucleotide comprising a sequence of nucleotides encoding a truncated human HER2ECDTM protein (SEQ ID NO:14), the polynucleotide sequence comprising codons optimized for expression in a human host. A particularly preferred polynucleotide of the present invention comprises a sequence of nucleotides as set forth in SEQ ID NO:9.

The present invention also relates to a synthetic nucleic acid molecule (polynucleotide) comprising a sequence of nucleotides which encodes mRNA that expresses a human HER2 protein, for example, the full-length human HER2 protein as set forth in SEQ ID NO:2, or a truncated HER2ECDTM protein, for example the HER2ECDTM sequence as set forth in SEQ ID NO:14. The synthetic nucleic acid molecules of the present invention are codon-optimized for high-level expression in a human host cell.

Also included within the scope of the present invention are codon-optimized polynucleotides comprising a sequence of nucleotides that encode a variant HER2 polypeptide that has at least 90% identity to the amino acid sequence of SEQ ID NO:2, which may include up to $N_a$ amino acid alterations over the entire length of SEQ ID NO:2, wherein $N_a$ is the maximum number of amino acid alterations, and is calculated by the formula $$N_a = X_a - (X_a Y),$$

in which $X_a$ is the total number of amino acids in SEQ ID NO:2, and Y has a value of 0.90, wherein any non-integer product of $X_a$ and Y is rounded to the nearest integer prior to subtracting such product from $X_a$. Likewise, the present invention also contemplates codon-optimized nucleotide sequences encoding variants of the HER2ECDTM polypeptide as set forth in SEQ ID NO:14.

The present invention also relates to recombinant vectors and recombinant host cells, both prokaryotic and eukaryotic, which contain the nucleic acid molecules disclosed throughout this specification. The synthetic DNA molecules, associated vectors, and hosts of the present invention are useful for the development of a cancer vaccine.

A preferred DNA molecule of the present invention comprises the nucleotide sequence disclosed herein as SEQ ID NO:1 (shown in FIG. 1), which encodes the human HER2 protein shown in FIG. 2 and set forth as SEQ ID NO:2. The nucleotide sequence set forth in SEQ ID NO:1 was codon-optimized for optimal expression in human cells. To avoid PCR amplification problems, in this embodiment of the present invention, a less stringent optimization design was adopted for the hHER2 sequence between position 3601 and 3805, which reduced GC content while preserving the same amino acid composition. See EXAMPLE 5.

An additional preferred DNA molecule of the present invention comprises the nucleotide sequence disclosed herein as SEQ ID NO:9 (shown in FIG. 6A), which encodes the human HER2ECDTM protein set forth as SEQ ID NO:14. The nucleotide sequence set forth in SEQ ID NO:9 was codon-optimized for optimal expression in human cells.

One of skill in the art will realize that other HER2 sequences may be designed which are codon-optimized for high-level expression in a human cell, provided that one or more codons are altered to human-preferred codons. It is preferred that at least about 80% of the codons comprising the synthetic HER2 nucleotide sequences of the present invention are human-preferred codons. It is more preferred that at least about 85% of the codons are human-preferred and even more preferred that at least about 90% of the codons are human-preferred.

The present invention also includes biologically active fragments or mutants of SEQ ID NO:1, which encode mRNA expressing human HER2 proteins. Any such biologically active fragment and/or mutant will encode either a protein or protein fragment which at least substantially mimics the pharmacological properties of the hHER2 protein, including but not limited to the hHER2 protein as set forth in SEQ ID NO:2. Any such polynucleotide includes but is not necessarily limited to: nucleotide substitutions, deletions, additions, amino-terminal truncations and carboxy-terminal truncations. The mutations of the present invention encode mRNA molecules that express a functional hHER2 protein in a eukaryotic cell so as to be useful in cancer vaccine development.

This invention also relates to synthetic codon-optimized DNA molecules that encode the hHER2 protein or the hHER2ECDTM protein, wherein the nucleotide sequence of the synthetic DNA differs significantly from the nucleotide sequence of SEQ ID NO:1 or SEQ ID NO:9, but still encodes the hHER2 protein as set forth in SEQ ID NO:2 or the hHER2ECDTM protein as set forth in SEQ ID NO:14. Such synthetic DNAs are intended to be within the scope of the present invention. Therefore, the present invention discloses codon redundancy that may result in numerous DNA molecules expressing an identical protein. Also included within the scope of this invention are mutations in the DNA sequence that do not substantially alter the ultimate physical properties of the expressed protein. For example, substitution of valine for leucine, arginine for lysine, or asparagine for glutamine may not cause a change in the functionality of the polypeptide.

It is known that DNA sequences coding for a peptide may be altered so as to code for a peptide that has properties that are different than those of the naturally occurring peptide. Methods of altering the DNA sequences include but are not limited to site directed mutagenesis. Examples of altered properties include but are not limited to changes in the affinity of an enzyme for a substrate or receptor for a ligand.

The present invention also relates to hHER2opt and hHER2ECDTMopt fusion constructs, including but not limited to fusion constructs which express a portion of the human HER2 protein linked to various markers, including but in no way limited to GFP (Green fluorescent protein), the MYC epitope, GST, and Fc. Any such fusion construct may be expressed in the cell line of interest and used to screen for modulators of the human HER2 protein disclosed herein. Also contemplated are fusion constructs that are constructed to enhance the immune response to human HER2 including, but not limited to: DOM, hsp70, and LTB.

The present invention further relates to recombinant vectors that comprise the synthetic nucleic acid molecules disclosed throughout this specification. These vectors may be comprised of DNA or RNA. For most cloning purposes, DNA vectors are preferred. Typical vectors include plasmids, modified viruses, baculovirus, bacteriophage, cosmids, yeast artificial chromosomes, and other forms of episomal or integrated DNA that can encode a hHER2 protein or a hHER2ECDTM protein. It is well within the purview of the skilled artisan to determine an appropriate vector for a particular gene transfer or other use.

An expression vector containing codon-optimized DNA encoding a HBER2 protein may be used for high-level expression of hHER2 in a recombinant host cell. Additionally, an expression vector containing codon-optimized DNA encoding a hHER2ECDTM protein may be used for high-level expression of hHER2ECDTM in a recombinant host cell. Expression vectors may include, but are not limited to, cloning vectors, modified cloning vectors, specifically designed plasmids or viruses. Also, a variety of bacterial expression vectors may be used to express recombinant hHER2 or hHER2ECDTM in bacterial cells if desired. In addition, a variety of fungal cell expression vectors may be used to express recombinant hHER2 or hHER2ECDTM in fungal cells. Further, a variety of insect cell expression vectors may be used to express recombinant protein in insect cells.

The present invention also relates to host cells transformed or transfected with vectors comprising the nucleic acid molecules of the present invention. Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines. Such recombinant host cells can be cultured under suitable conditions to produce hHER2, hHER2ECDTM, or a biologically equivalent form. In a preferred embodiment of the present invention, the host cell is human. As defined herein, the term "host cell" is not intended to include a host cell in the body of a transgenic human being, transgenic human fetus, or transgenic human embryos.

As noted above, an expression vector containing DNA encoding a hHER2 protein or a hHER2ECDTM protein may be used for expression of hHER2 or hHER2ECDTM in a recombinant host cell. Therefore, another aspect of this invention is a process for expressing a human HER2 protein or a human HER2ECDTM protein in a recombinant host cell, comprising: (a) introducing a vector comprising a codon-optimized nucleic acid that encodes human HER2 or human HER2ECDTM into a suitable human host cell; and, (b) culturing the host cell under conditions which allow expression of said human HER2 protein or said human HER2ECDTM protein.

A preferred embodiment of this aspect of this invention provides a process for expressing a human HER2 protein in a recombinant host cell, comprising: (a) introducing a vector comprising a nucleic acid as set forth in SEQ ID NO:1 into a suitable human host cell; and, (b) culturing the host cell under conditions which allow expression of said human HER2 protein.

Another preferred embodiment of this aspect of this invention provides a process for expressing a human HER2ECDTM protein in a recombinant host cell, comprising: (a) introducing a vector comprising a nucleic acid as set forth in SEQ ID NO:9 into a suitable human host cell; and, (b) culturing the host cell under conditions which allow expression of said human HER2ECDTM protein.

Following expression of hHER2 or hHER2ECDTM in a host cell, hHER2 or hHER2ECDTM protein may be recovered to protein in active form. Several protein purification procedures are available and suitable for use. Recombinant hHER2 protein or HER2ECDTM protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant protein can be separated from other cellular proteins by use of an immunoaffinity column made with monoclonal or polyclonal antibodies specific for full-length hHER2 protein, or polypeptide fragments of hHER2 protein.

The nucleic acids of the present invention may be assembled into an expression cassette which comprises sequences designed to provide for efficient expression of the protein in a human cell. In one embodiment of the invention, the cassette contains a full-length codon-optimized hHER2 gene, with related transcriptional and translations control sequences operatively linked to it, such as a promoter, and termination sequences. In a second embodiment of the invention, the cassette contains a truncated HER2 gene, HER2ECDTM, which encodes the extracellular and transmembrane domains of the human HER2 protein. In preferred embodiments, the promoter is the cytomegalovirus promoter without the intron A sequence (CMV), although those skilled in the art will recognize that any of a number of other known promoters such as a strong immunoglobulin, or other eukaryotic gene promoter may be used. A preferred transcriptional terminator is the bovine growth hormone terminator, although other known transcriptional terminators may also be used. The combination of CMV-BGH terminator is particularly preferred.

In accordance with this invention, the hHER2opt or hHER2ECDTMopt expression cassette is inserted into a vector. The vector is preferably an adenoviral vector, although linear DNA linked to a promoter, or other vectors, such as adeno-associated virus or a modified vaccinia virus, retroviral or lentiviral vector may also be used.

If the vector chosen is an adenovirus, it is preferred that the vector be a so-called first-generation adenoviral vector. These adenoviral vectors are characterized by having a non-functional E1 gene region, and preferably a deleted adenoviral E1 gene region. In some embodiments, the expression cassette is inserted in the position where the adenoviral E1 gene is normally located. In addition, these vectors optionally have a non-functional or deleted E3 region. It is preferred that the adenovirus genome used be deleted of both the E1 and E3 regions ($\Delta E1\Delta E3$). The adenoviruses can be multiplied in known cell lines which express the viral E1 gene, such as 293 cells, or PERC.6 cells, or in cell lines derived from 293 or PERC.6 cell which are transiently or stably transformed to express an extra protein. For examples, when using constructs that have a controlled gene expression, such as a tetracycline regulatable promoter system, the cell line may express components involved in the regulatory system. One example of such a cell line is T-Rex-293; others are known in the art.

For convenience in manipulating the adenoviral vector, the adenovirus may be in a shuttle plasmid form. This invention is also directed to a shuttle plasmid vector which comprises a plasmid portion and an adenovirus portion, the adenovirus portion comprising an adenoviral genome which has a deleted E1 and optional E3 deletion, and has an inserted expression cassette comprising codon-optimized human HER2 or codon-optimized hHER2ECDTM. In preferred embodiments, there are restriction sites flanking the adenoviral portion of the plasmid so that the adenoviral vector can easily be removed. The shuttle plasmid may be replicated in prokaryotic cells or eukaryotic cells.

In a preferred embodiment of the invention, the expression cassette is inserted into the pMRKAd5-HV0 adenovirus plasmid (See Emini et al., WO 02/22080, which is hereby incorporated by reference). This plasmid comprises an Ad5 adenoviral genome deleted of the E1 and E3 regions. The design of the pMRKAd5-HV0 plasmid was improved over prior adenovectors by extending the 5' cis-acting packaging region further into the E1 gene to incorporate elements found to be important in optimizing viral packaging, resulting in enhanced virus amplification. Advantageously, this enhanced adenoviral vector is capable of maintaining genetic stability following high passage propagation.

Standard techniques of molecular biology for preparing and purifying DNA constructs enable the preparation of the adenoviruses, shuttle plasmids, and DNA immunogens of this invention.

It has been determined in accordance with the present invention that the synthetic cDNA molecules described herein (e.g. SEQ ID NO:1 and SEQ ID NO:9), which are codon-optimized for high-level expression in a human cell, are expressed with greater efficiency than the corresponding wild type sequence. Additionally, it was shown herein that hHER2opt is more immunogenic that hHER2 and is more efficient in eliciting both cellular and humoral immune responses.

Therefore, the vectors described above may be used in immunogenic compositions and vaccines for preventing the development of adenocarcinomas associated with aberrant HER2 expression and/or for treatment of existing cancers. The vectors of the present invention allow for vaccine development and commercialization by eliminating difficulties with obtaining high expression levels of exogenous HER2 in successfully transformed host organisms. To this end, one aspect of the instant invention is a method of preventing or treating HER2-associated cancer comprising administering to a mammal a vaccine vector comprising a synthetic codon-optimized nucleic acid molecule, the synthetic codon-optimized nucleic acid molecule comprising a sequence of nucleotides that encodes a human HER2 protein as set forth in SEQ ID NO:2 or a human HER2ECDTM protein as set forth in SEQ ID NO:14.

In accordance with the method described above, the vaccine vector may be administered for the treatment or prevention of cancer in any mammal. In a preferred embodiment of the invention, the mammal is a human.

Further, one of skill in the art may choose any type of vector for use in the treatment and prevention method described. Preferably, the vector is an adenovirus vector or a plasmid vector. In a preferred embodiment of the invention, the vector is an adenoviral vector comprising an adenoviral genome with a deletion in the adenovirus E1 region, and an insert in the adenovirus E1 region, wherein the insert comprises an expression cassette comprising: (a) a synthetic codon-optimized polynucleotide encoding a human HER2 protein or a human HER2ECDTM protein; and (b) a promoter operably linked to the polynucleotide.

The instant invention further relates to an adenovirus vaccine vector comprising an adenoviral genome with a deletion in the E1 region, and an insert in the E1 region, wherein the insert comprises an expression cassette comprising: (a) a synthetic codon-optimized polynucleotide encoding a human HER2 protein or a human HER2ECDTM protein; and (b) a promoter operably linked to the polynucleotide.

In a preferred embodiment of this aspect of the invention, the adenovirus vector is an Ad 5 vector.

In other preferred embodiments of the invention, the vector is an Ad6 vector or an Ad24 vector.

In another aspect, the invention relates to a vaccine plasmid comprising a plasmid portion and an expression cassette portion, the expression cassette portion comprising: (a) a synthetic codon-optimized polynucleotide encoding a human HER2 protein; and (b) a promoter operably linked to the polynucleotide.

The invention also relates to a vaccine plasmid comprising a plasmid portion and an expression cassette portion, the expression cassette portion comprising: (a) a synthetic codon-optimized polynucleotide encoding a human HER2ECDTM protein; and (b) a promoter operably linked to the polynucleotide.

In some embodiments of this invention, the recombinant adenovirus vaccines disclosed herein are used in various prime/boost combinations with a plasmid-based polynucleotide vaccine in order to induce an enhanced immune response. In this case, the two vectors are administered in a "prime and boost" regimen. For example the first type of vector is administered, then after a predetermined amount of time, for example, 2 weeks, 1 month, 2 months, six months, or other appropriate interval, a second type of vector is administered. Preferably the vectors carry expression cassettes encoding the same polynucleotide or combination of polynucleotides. In the embodiment where a plasmid DNA is also used, it is preferred that the vector contain one or more promoters recognized by mammalian or insect cells. In a preferred embodiment, the plasmid would contain a strong promoter such as, but not limited to, the CMV promoter. The synthetic human HER2 gene, HER2ECDTM gene, or other gene to be expressed would be linked to such a promoter. An example of such a plasmid would be the mammalian expression plasmid V1Jns as described (J. Shiver et. al. in *DNA Vaccines*, M. Liu et al. eds., N.Y. Acad. Sci., N.Y., 772:198-208 (1996), which is herein incorporated by reference).

As stated above, an adenoviral vector vaccine and a plasmid vaccine may be administered to a vertebrate as part of a single therapeutic regime to induce an immune response. To this end, the present invention relates to a method of protecting a mammal from cancer comprising: (a) introducing into the mammal a first vector comprising: i) a synthetic codon-optimized polynucleotide encoding a human HER2 protein or a human HER2ECDTM; and ii) a promoter operably linked to the polynucleotide; (b) allowing a predetermined amount of time to pass; and (c) introducing into the mammal a second vector comprising: i) a synthetic codon-optimized polynucleotide encoding a human HER2 protein or a human HER2ECDTM; and ii) a promoter operably linked to the polynucleotide.

In one embodiment of the method of protection described above, the first vector is a plasmid and the second vector is an adenovirus vector. In an alternative embodiment, the first vector is an adenovirus vector and the second vector is a plasmid.

The instant invention further relates to a method of treating a mammal suffering from a HER2-associated cancer comprising: (a) introducing into the mammal a first vector comprising: i) a synthetic codon-optimized polynucleotide encoding a human HER2 protein or a human HER2ECDTM protein; and ii) a promoter operably linked to the polynucleotide; (b) allowing a predetermined amount of time to pass; and (c) introducing into the mammal a second vector comprising: i) a synthetic codon-optimized polynucleotide encoding a human HER2 protein or a human HER2ECDTM protein; and ii) a promoter operably linked to the polynucleotide.

In one embodiment of the method of treatment described above, the first vector is a plasmid and the second vector is an adenovirus vector. In an alternative embodiment, the first vector is an adenovirus vector and the second vector is a plasmid.

The amount of expressible DNA or transcribed RNA to be introduced into a vaccine recipient will depend partially on the strength of the promoters used and on the immunogenicity of the expressed gene product. In general, an immunologically or prophylactically effective dose of about 1 ng to 100 mg, and preferably about 10 μg to 300 μg of a plasmid vaccine vector is administered directly into muscle tissue. An effective dose for recombinant adenovirus is approximately $10^6$-$10^{12}$ particles and preferably about $10^7$-$10^{11}$ particles. Subcutaneous injection, intradermal introduction, impression though the skin, and other modes of administration such as intraperitoneal, intravenous, or inhalation delivery are also contemplated. It is also contemplated that booster vaccinations may be provided. Parenteral administration, such as intravenous, intramuscular, subcutaneous or other means of administration with adjuvants such as interleukin 12 protein, concurrently with or subsequent to parenteral introduction of the vaccine of this invention is also advantageous.

The vaccine vectors of this invention may be naked, i.e., unassociated with any proteins, adjuvants or other agents which impact on the recipient's immune system. In this case, it is desirable for the vaccine vectors to be in a physiologically acceptable solution, such as, but not limited to, sterile saline or sterile buffered saline. Alternatively, it may be advantageous to administer an immunostimulant, such as an adjuvant, cytokine, protein, or other carrier with the vaccines or immunogenic compositions of the present invention. Therefore, this invention includes the use of such immunostimulants in conjunction with the compositions and methods of the present invention. An immunostimulant, as used herein, refers to essentially any substance that enhances or potentiates an immune response (antibody and/or cell-mediated) to an exogenous antigen. Said immunostimulants can be administered in the form of DNA or protein. Any of a variety of immunostimulants may be employed in conjunction with the vaccines and immunogenic compositions of the present inventions, including, but not limited to: GM-CSF, IFNα, tetanus toxoid, IL12, B7.1, LFA-3 and ICAM-1. Said immunostimulants are well-known in the art. Agents which assist in the cellular uptake of DNA, such as, but not limited to calcium ion, may also be used. These agents are generally referred to as transfection facilitating reagents and pharmaceutically acceptable carriers. Those of skill in the art will be able to determine the particular immunostimulant or pharmaceutically acceptable carrier as well as the appropriate time and mode of administration.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

The following examples illustrate, but do not limit the invention.

EXAMPLE 1

Human HER2 Optimized Codon Sequence

The entire hHER2.opt coding sequence was synthesized and assembled by BIONEXUS (Bionexus Inc. Oakland Calif.) and cloned into the pCR-blunt vector (Invitrogen, The Netherlands). The hHER2.opt cDNA was constructed using oligonucleotides and assembled by PCR. For many experiments described herein, the hHER2.opt nucleotide sequence used carried an optimized Kozak sequence at its 5'-end, the complete nucleotide sequence as set forth in SEQ ID NO:11.

In addition, the ATP binding Lysine residue 753 was substituted with Alanine (K753A) by replacing codon AAA with GCA. This mutation abrogates tyrosine kinase activity of the corresponding protein and eliminates the downstream signaling events and resulting oncogenic activity of human (Messerle et al. *Mol Cell Endocrinol* 105(1): 1-10 (1994)) or rat HER2 (Ben Levi et al., supra). In addition, the kinase-deficient K756A mutant can inactivate the signaling activity of a co-expressed oncogenic hHER2.wt.

EXAMPLE 2

Plasmid Constructs pV1J-hHER2.wt: The human HER2 wild type coding sequence was amplified by PCR from plasmid pLTR-2/erbB2 (kindly provided by P. Di Fiore, European Institute of Oncology, Milan, Italy; Di Fiore et al. *Science* 237 (4811): 178-82 (1987)) using primers hNeu. for 1 (5'-CCAGTT-TAAACATTTAA ATGCCGCCACCATGGAGCTGGCGGCCT-3'; (SEQ ID NO:3 coding sequence is underlined) and hNeu.rev2 (5'-GCC GTCGACTTTACACTGGCACGTCCAGACCCA-3' ((SEQ ID NO:4) and TaKaRa LA Taq polymerase (TaKaRa Otsu, Shiga, Japan). The amplification product, which incorporates an optimized translation start site (Kozak, M., *J Mol Biol* 196(4): 947-50 (1987); Kozak, M., *Nucleic Acids Res* 15(20): 8125-48 (1987)), was digested with PmeI and SalI restriction enzymes and cloned into the EcoRV and SalI sites of mammalian expression plasmid pV1JnsA (see Montgomery et al. *DNA Cell Biol* 12(9): 777-83 (1993)). The plasmid pV1J-hHER2 thus generated contained the full-length wild type human HER2 sequence under the transcriptional control of the human cytomegalovirus immediate-early promoter with its intron A sequence. The human wild type HER2 coding sequence was followed by the bovine growth hormone polyadenylation signal sequence.

pV1J-hHER2.opt: A 3793 bp EcoRI-SalI fragment was excised from plasmid pCR-hHER2opt and cloned into the corresponding sites of plasmid pV1JnsB (Montgomery et al., supra) generating the pV1J-hHER2.opt plasmid.

pV1J-hHER2ECDTM.opt: A 2168 bp fragment was amplified by PCR using TaKaRa taq) with primers EcoRV-for (5'-CCAGATATCGAATTCTAGAGCCGCCACCATGGA-3' (SEQ ID NO:12)) and SalI-rev (5'-GCTGTCGACTTTAT-CAGATCAGGATGCCCGAACACCACGCCC-3' (SEQ ID NO:13)) from pV1J-hHER2.opt. The resulting fragment was digested with the EcoRV and SalI restriction enzymes and cloned into the corresponding sites of plasmid pV1JnsB (Montgomery et al., supra) generating the pV1J-hHER2ECDTM.opt plasmid.

EXAMPLE 3

Codon Optimized hHER2 cDNA

A synthetic human HER2 gene (hHER2.opt, FIG. 1) was designed to incorporate human-preferred (humanized) codons for each amino acid (hereinafter aa) residue. During assembly of the gene, PCR amplification consistently deleted an 86 bp sequence starting from position 3642, due to the high GC content of the sequence in this region. To overcome this problem, a less stringent optimization design was adopted for the hHER2 sequence between position 3601 and 3805, which reduced GC content while preserving the same aa composition.

The codon optimized cDNA was modified to maintain 83.9% nucleotide identity to the original clone. The codon optimized cDNAs were cloned into the pV1J vectors (Montgomery et al., supra), placing in front a Kozak optimized sequence (5'-GCCGCCACC-3', SEQ ID NO:8) and under the control of the human cytomegalovirus (CMV)/intron A promoter plus the bovine growth hormone (BGH) termination signal. The construct was named pV1J-hHER2opt (see EXAMPLE 2).

EXAMPLE 4

In Vitro Expression of Plasmid Constructs

The in vitro expression of the pV1J-hHER2.wt and pV1J.hHER2.opt constructs was assessed by transiently transfecting human embryonic kidney HEK-293 or mouse myoblasts C2C7 cell lines and detecting human HER2 expression by flow cytometry. Supercoiled, endotoxin-free plasmid DNA pV1J-hHER2-wt encoding the human HER2 expression cassette used for immunization was purified from *E. coli* DH12S cells (Invitrogen, Groningen, The Netherlands) by Qiagen endo-free plasmid Giga Kit (Qiagen, Hilden, Germany).

Plasmids pV1J-hHER2.wt or pV1J-hHER2.opt were lipofectamine-transfected (Gibco BRL Invitrogen, Groningen, The Netherlands) in HEK-293 cells. Similarly, mouse myoblasts C2C7 cells were transfected with a 1:1 or 10:1 mixture of plasmid pHygEGFP (BD Biosciences Clontech, Palo Alto, Calif.) and pV1J-hHER2.wt or pV1J-hHER2.opt.

Figure 3B:
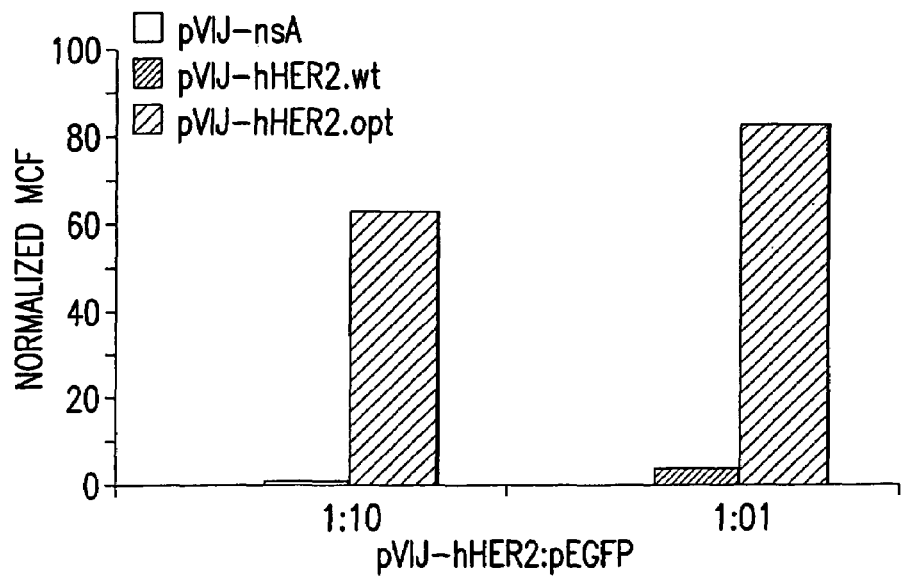

In vitro transfection of HEK-293 or C2.7 cells showed that the codon optimized sequence dramatically improves hHER2 expression compared to the wt sequence (FIGS. 3A and 3B).

EXAMPLE 5

Mice Immunization

Six-week old inbred female BALB/c mice (H-$2^d$; kindly provided by G. Formi, University of Turin) were kept in standard conditions. Mice were treated in accordance with European union and institutional guidelines. In particular, mice were fully anesthetized with ketamine (Imalgene 500; Merial Italia, Milano, Italy) at 100 mg/kg of body weight and xylazine (Xilor, BIO 98; S. Lazzaro, Bologna, Italy) at 5.2 mg/kg when necessary for procedures.

Fifty micrograms of plasmid DNA were electroinjected in a 50 μl volume in mice quadriceps at 6, 8, and 10 weeks of age, as previously described (Rizzuto et al. *Proc. Natl. Acad. Sci. U.S.A.* 96(11): 6417-22 (1999)). 50 μg of pCMV hNeu optimized or not were injected without incising the skin into both quadriceps muscles (25 μg in 50 μl of physiologic solution/injection) and electrostimulation (ES) was performed as previously described (Zucchelli et al. *J. Virol.* 74(24): 11598-607 (2000); Rizzuto et al., supra). Briefly, electrical shock consisted of 10 trains with 1000 bipolar pulses (130V, 75 mA, 200 μs/phase).

Ad injections were carried out in mice quadriceps in 50 μl volumes. Sera were collected at 7 wks (1 wk before first immunization, pre-bleed), and 12 wks (two weeks after the last immunization).

EXAMPLE 6

Mouse IFN-γ ELISPOT Assay

Mouse splenocytes secreting IFN-γ in an antigen-specific manner were detected using a standard enzyme-linked immunospot (ELISPOT) assay (Miyahira et al. *J Immunol Methods* 181(1): 45-54 (1995)). Multiscreen 96-well MAIP filtration plates (cat. No. MAIPS4510; Millipore, Bedford, Mass.) were coated with an affinity-purified rat anti-mouse IFN-γ antibody ((IgG1, clone R4-6A2, cat No. 18181D, Pharmingen, San Diego, Calif.) diluted sterile PBS. After overnight incubation, plates were washed with PBST (0.005% Tween in PBS) and incubated with R10 medium for 2 hrs at 37° C. to block non-specific binding.

Splenocytes were obtained by removing the spleen from euthanized mice in a sterile manner. Spleen disruption was carried out by grating the dissected spleen on a metal grid. Red blood cells were removed by osmotic lysis by adding 1 ml of 0.1× PBS to the cell pellet and vortexing no more than 15 seconds. One ml of 2× PBS was then added and the volume was brought to 4 ml with 1× PBS. Cells were pelleted by centrifugation at 1200 rpm for 10 min at room temp., and the pellet was resuspended in 1 ml R10 medium (RPMI 1640 supplemented with 10% fetal calf serum, 2 mM L-glutamine, 50 U of penicillin per ml, 50 μg of streptomycin per ml, 10 mM HEPES, 50 μM 2-mercaptoethanol). Viable cells were counted using Turks staining.

Splenocytes derived from the spleen of two or more immunized mice were incubated for 15 hrs in the presence of 6 μg/ml of a single or a pool of peptides, at a density of 2.5-5 $10^5$ cells/well. Concanavalin A (ConA) was used as positive internal control for each mouse at 5 μg/ml. After extensive washing with PBST, biotinylated rat anti-mouse IFN-gamma antibody (cat No. 18112D, PharMingen; San Diego, Calif.) was added. The plates were incubated at 4° C. overnight and then washed with PBST prior to the addition of streptavidin-alkaline phosphatase (Cat No. 13043E, PharMingen; San Diego, Calif.). After incubation for 2 hrs at room temperature the plates were extensively washed with PBST and developed by incubating with a one-step nitroblue tetrazolium-5-bromo-4-chloro-3-indolylphosphate substrate (cat. No. 34042, Pierce, Rockford, Ill.) for 5 to 15 min for development of spots. Rinsing the plates in water stopped the reaction. DMSO and Concanavalin A (10 μg/ml) were included as background and positive control for each sample. Spots were counted by computer-assisted imaging analysis (AID ELR02 coupled with AID ELISPOT 2.6 Software, Strassberg, Germany).

The frequency of positive IFN-γ producing splenocytes per total number of cells plated per well was calculated as the average value of spots derived from duplicates at two different cell concentrations subtracted of the average value similarly derived from spots measured in control wells containing non-pulsed splenocytes. Changes in frequency of IFN-γ producing cells were defined as exceeding a 95% confidence bound calculated from measurements of controls. Differences with a p value <0.05 were considered significant.

EXAMPLE 7

Identification of Immunodominant T-Cell Epitopes in the Human HER2 Protein

Three hundred and twelve 15-amino acid peptides, overlapping by 11 amino acids, were designed to span the entire human HER2 sequence. These peptides, which also included seven peptides designed to overcome insolubility problems, were synthesized by SynPep (Dublin, Calif.). All peptides were shown to be >90% pure by HPLC and were used without HPLC purification. Peptides were reconstituted at 35 mg/ml in DMSO. Those peptides that did not immediately dissolve were rocked at 37° C. to aid dissolution. If necessary, 1 to 3 additional volume(s) of DMSO were added to fully dissolve those peptides that were still not in solution after several hours of rocking. Reconstituted peptides were combined so that each peptide was equally represented in the mix. The final concentration of each peptide in the mix was calculated to be 1 mg/ml. Each mix was aliquoted and stored at 80° C.

To identify the immunodominant T-cell epitopes of the human HER2 gene in BALB/c mice (H-$2^d$ genetic background), 6-week-old female BALB/c mice were immunized by injecting $10^9$ vp of Ad5-hHER2 in the quadriceps muscles. A second injection was performed after 3 weeks. A second group of mice was similarly injected with saline solution as negative control. Three weeks after the second injection, the animals were sacrificed and the frequency of IFN-γ secreting T cells in mouse splenocytes was evaluated by interferon-γ enzyme-linked immunospot (IFN-γ ELISPOT) assay.

Three hundred and eleven peptides, each 15 amino acids long, overlapping by 11 residues, and spanning the entire human HER2 protein sequence were combined into eleven pools indicated with alphabetical letters from A to K, from N- to C-terminus. Each of these pools was tested for its ability to stimulate IFN-γ spleen T cells. For peptide pools A, B and M, IFN-γ ELISPOT measured a statistically significant IFN-γ production by mice immunized with Ad5-hHER2 as compared to control in the absence of peptide. To identify the individual peptide responsible for the activity, peptides from pool A, B and M were divided into sub-pools, among which $A_{III}$ and $A_{IV}$, $B_{III}$ and $M_I$ scored positive. Single peptides from these positive subpools were then tested for their ability to trigger IFN-γ release. Overlapping peptides hNeu-15 and hNeu-16 exhibited high and comparable reactivity. A much lower reactivity was exhibited by overlapping peptides hNeu-41 and hNeu-42. Another peptide, hNeu-301, was also shown to contain a T-cell epitope.

To confirm these data and identify the CD4+ or CD8+ T cell subset responsible for IFN-γ production, IFN-γ secreting T-cells were characterized by intracellular staining (ICS). Mouse splenocytes were incubated with single peptides for 12 hrs in the presence of the secretion inhibitor brefeldin A, fixed, permeabilized and then stained for intracellular IFN-γ, CD3 and CD4 or CD8 markers and analyzed by flow cytometry. ICS confirmed the reactivity of peptide hNeu-15, identifying it as an epitope able to activate $CD8^+$ cells. Peptide hNeu15 and hNeu16 were equally reactive in ELISPOT analysis, suggesting that the $CD8^+$ epitope should be comprised in the 11 aa residues common to the two peptides.

To identify the target nonamer sequence, we tested three 9 aa-long peptides spanning the overlapping region between hNeu15 and hNeu16. hNeu15.3 proved the most reactive, displaying a slightly increased reactivity compared to the 15 aa long peptides hNeu-15 and hNeu-16. Interestingly, about half of the reactivity was also detected with hNeu15.1, indicating that two overlapping but distinct $CD8^+$ epitopes co-exist in this 11 aa sequence.

IFN-γ ICS analysis also confirmed the reactivity of hNeu301 and typed it as a $CD8^+$ epitope. Analysis of these $CD8^+$ epitopes by IFN-γ ELISPOT confirmed the results obtained by ICS. Finally, a low reactivity was detected for hNeu41 and hNeu42 peptides, whose low response was predominantly CD4+.

EXAMPLE 8

Intracellular Cytokine Staining

Intracellular IFN-γ production was measured according to BD Pharmingen standard protocol. Briefly, $2 \times 10^6$ spleen cells were cultured for 15 hrs in R10 medium in the presence of 6 μg/ml of single or pool of peptides and Brefeldin A as protein transport inhibitor (Cytofix/Cytoperm Plus™ with Golgi-Plug™ Kit; BD Pharmingen; San Diego, Calif.). *Staphylococcus* Enterotoxin B (SEB) at 10 μg/ml (cat. No. S4881, SIGMA, Saint Louis, Mich.) and DMSO were tested with the splenocytes as positive and background control, respectively.

Before staining of surface antigens, Ab anti-mouse CD16/ CD32 was used to reduce non-specific immunofluorescent signal (cat No. 553142, BD PharMingen, San Diego, Calif.). The specific signal was obtained with APC-anti-mouse CD3e, PE-anti-mouse CD4 and PerCP-anti-mouse CD8a (cat. No. 553066, 553653 and 553036, BD Pharmingen; San Diego, Calif.). The cells were then washed, fixed, permeabilized, and stained for intracellular IFN-γ using FITC-conjugated mAb (cat. No. 554411, BD Pharmingen San Diego, Calif.). T lymphocyte IFN-γ was calculated as $1000 \times [(IFN-\gamma^+, CD3^+ \text{ and } CD4^+ \text{ or } CD8^+)/(CD3^+ \text{ and } CD4^+ \text{ or } CD8^+)]$. Generally, at least 50,000 $CD3^+$ lymphocytes were collected by simultaneously gating on $CD3^+$ events and small lymphocytes. All samples were acquired within 24 hrs of staining using a FACSCalibur flow cytometer and CellQuest software (Becton Dickinson, San Jose, Calif.).

EXAMPLE 9

Antibody Titration and Isotyping

Sera for antibody titration were obtained by retro-orbital bleeding. ELISA plates (Nunc Maxisorp™, Roskilde, Denmark) were coated overnight at 4° C. with goat anti-human IgG Fc-specific (Pierce; Cat. no. 31123) at a concentration of 2 μg/ml in 50 mM $NaHCO_3$ (pH 9.6). Excess of antibody was removed and non-specific binding blocked by incubating for 60 min at 37° C. in PBBST5 buffer (BSA 5%. Tween 0.05%). After washing, supernatant of IgB2-cells was added in saturating condition and incubated at RT for 2 hrs (Chen et al. *J Biol Chem* 271(13): 7620-9 (1996)). IgB2 cells (kindly provided by Dr. Y. Yarden, Weizmann Institute of Science, Rehovot, Israel) are HEK-293 cells secreting the dimeric fusion between the extracellular domain of HER2 and the Fc portion of human Ig. Plates were washed and serial dilution of sera (from 1:4,000 to 1:25,600) in PBBST1 buffer (BSA 1%, Tween 0.05%) were incubated overnight at 4° C. Pre-immune sera were used as background. Washes were carried out with PBBST1. Secondary antibody (goat anti-mouse IgG1 or IgG2a AP-conjugated (Pharmingen, 557272 and 553389) was diluted 1:40,000 in PBBST5 and incubated 2-3 hr at room temp. on a shaker. After washing, plates were developed by incubation with Sigma 106 phosphatase substrate (Sigma; cat. no. A106) in diethanolamine. Plates were read by an automated ELISA reader (Labsistems Multiskan Bichromatic, Helsinki, Finland) and the results were expressed as $A = A_{405nm} - A_{620nm}$. For each sample, the background signal detected with the pre-immune serum was subtracted.

Anti-hHER2 serum titers were calculated as the reciprocal limiting dilution of serum producing an absorbance at least 3-fold greater than the absorbance of autologous pre-immune serum at the same dilution.

EXAMPLE 10

Increased Immunogenicity of hHER2opt

To examine in vivo immune responses induced by the wild type and codon optimized hHER2 expression vectors, BALB/c mice were immunized intramuscularly with pV1J-hHER2.wt or pV1J-hHER2.opt plasmid DNA followed by ES (as described in EXAMPLE 5). Mice were subjected to three injections at 6, 8, and 10 weeks of age. Two weeks after the last immunization, splenocytes were isolated from each mouse. To quantify the IFNγ-secreting hHER2-specific CD8 T-cell precursor frequencies generated by the plasmid DNA immunization, the ELISPOT assay for the $H-2^d$ restricted T-cell epitope hNeu15.3 and hNeu42 was used. Immunization with the HER2 wild-type sequence elicited a barely detectable CD8+ response, and reactivity with the CD4+ peptide was absent. In contrast, the optimized HER2 sequence induced a 10-fold enhanced response to the CD8+ peptide, yielding up to 286 IFNγ spot forming cells (SFC, mean value) specific for the tested epitopes. A lower CD4+ activity was also detected. No peptide-specific IFN γ SFC were detected in the pV1J-nsB-immunized mice (data not shown).

Sera from the same mice were tested by ELISA using the IgB2 protein as substrate (FIG. 4B). The hHER2-specific antibody titer was detected in all pV1J-hHER2.opt-immunized mice and the geometric mean value of the Ab titer was 46,000 or 78,000 for IgG1 or IG2a. In contrast, the pV1J-hHER2.wt immunized group showed an approximately 100-fold lower geometric mean titer of hHER2-specific antibody. Thus, these results demonstrate that the codon optimized cDNA of hHER2 is more efficient in eliciting a cellular and humoral immune response than the wild-type sequence.

EXAMPLE 11

Adenovirus Vectors

MRKAd5-hHER2.wt: A SwaI-SalI DNA fragment from pV1J_hHER2 containing the human HER2 cDNA was cloned in the corresponding sites of the shuttle plasmid polyMRKΔE1 (Bett et al., *Proc Natl Acad Sci USA* 91(19): 8802-04 (1994)). The resulting plasmid pMRKΔE1_hHER2 contained a human CMV promoter driving the expression of the human HER2 cDNA, followed by the bovine growth hormone polyadenylation signal. Plasmid pMRKΔE1_hHER2 was recombined with the adenoviral backbone plasmid pAd5_HV0 to generate the pre-adenoviral plasmid pAd5-hHER2 wt.

MRKAd5-hHER2ECDTM.opt: Plasmid pCR-hHER2opt was digested with EcoRI. The resulting 2156 bp insert was purified and cloned into the EcoRI of the polyMRK-Ad5 shuttle plasmid (See Emini et al., WO 02/22080, which is hereby incorporated by reference).

Plasmids pAd5-hHER2.wt and pMRKAd5-hHER2.opt were linearized by PacI digestion and transfected into PerC6 cells to generate Ad5-hHER2 recombinant adenovirus. The viruses were grown in large quantities by multiple rounds of amplification and purified by caesium chloride gradient ultracentrifugation (Fallaux et al., *Hum Gene Ther* 9(13): 1909-17 (1998)). Viral DNA was extracted by proteinase K digestion and genomic integrity was confirmed by restriction analysis.

HEK 293 cells were infected with MRKAd5-hHER2.wt or MRKAd5-hHER2ECDTM.opt using various multiplicity of infection (m.o.i.). Expression monitored by western blot analysis revealed more than a 10-fold difference between the truncated protein expressed from the codon-optimized sequence compared to the full length protein expressed from the wt HER2 sequence (data not shown).

EXAMPLE 12

Comparison of Immunization Regimens

The efficiency in inducing an anti-human HER2 cell-mediated immune response of Adenovirus was compared with that of plasmid DNA associated with electrical stimulation, both harboring a CMV-HER2 expression cassettes. Fifty μg of plasmid pV1J-HER2 were injected into the quadriceps muscle of wt BALB/c mice or BALB/c transgenic mice overexpressing rat HER2 (indicated as NeuT, see Lucchini et al., *Cancer Lett* 64(3): 203-9 (1992)) followed by ES at 6 and 9 weeks of age. Two weeks after boosting, animals were sacrificed and spleen cells were collected and stimulated with peptides containing the immunodominant p185 epitopes. Very low spot forming cells (SFC) were detected following stimulation with human peptides, both in BALB/c and neuT mice (FIG. 5). On average, the response was 50-fold lower than that induced by Ad5-HER2 immunization. The above data show that immunizing mice with plasmid pV1J-HER2 induced a comparable response in BALB/c and neuT mice for each protocol.

EXAMPLE 13

Immunization of rhesus Macaques with Human HER2 in Combination with Human CEA and EpCAM Antigens To assess the efficiency of immunization of rhesus macaques (macaca mulatta) with the human tumor antigen HER2 in combination with other tumor antigens, a group of 4 rhesus monkeys (2 males and 2 females) were immunized with a mixture of plasmid DNA vectors expressing codon optimized sequences of human tumor antigens Ep-CAM, CEA, and HER2/neu.

Immunization studies were performed at the Biomedical Primate Research Centre (BPRC, Rijswijk, The Netherlands). These immunization studies were designed to evaluate the T cell responses induced by the human antigens against the rhesus homologues of the same antigens.

Monkeys were vaccinated intramuscularly with injections at weeks 0, 2, 4, 6, 8, 10, 12, 14, and 16, followed by electro-stimulation. Animals were injected under anesthesia with 1 ml solution (split over 2 sites with 0.5 ml/site) containing 6 mg plasmid DNA for animals weighing 2-5 kilos.

For electrostimulation, 2 trains of 100 square bipolar pulses (1 sec each), were delivered every other second for a total treatment time of 3 sec. The pulse length was 2 msec/phase with a pulse frequency and amplitude of 100 Hz and 100 mA (constant current mode), respectively.

The same monkeys were then vaccinated at weeks 27 and 31 with a mixture of three Adenovirus 5 (ΔE1-ΔE3, "first generation", P2 level) expressing the wt sequence of human HER2, human CEA or human EpCAM, respectively.

To measure the immune response to rhesus homologue of human HER2 using the above immunization protocol, blood samples were collected every four weeks for a total duration of one year. The cell-mediated immune response was measured by IFNγ Elispot assay. Results reported in FIG. 7 indicate that the immunization protocol discussed above was effective in inducing a specific immune response against endogenous rhesus homologue of human HER2/neu.

EXAMPLE 14

Comparison of p185-Specific T-Cell Response Elicited in Mice by Immunization with pV1J-HER2opt and pV1J-HER2ECDTM.opt The immunization efficiency of a C-terminal deletion mutant of p185 retaining the extra-cellular and the transmembrane domain (HER2ECDTM) was evaluated. Plasmid DNA expressing the codon-optimized sequence of the full length (pV1J-HER2.opt) or of the truncated protein (pV1J-HER2ECDTM.opt) was electro-injected at weeks 10 and 12, and analysis was performed at week 14. The truncated protein HER2ECDTM induced an anti-p185 cell-mediated response higher than that induced by the full length p185 protein, both as CD4+ and CD8+ reactivity, as measured by IFN-gamma ELISPOT analysis (FIG. 8). In vitro expression analysis in C2.7 murine myoblasts did not reveal differences in the expression between the two plasmids (data not shown).

What is claimed is:

1. A synthetic nucleic acid molecule comprising a sequence of nucleotides that encodes a human HER2ECDTM protein, the synthetic nucleic acid molecule being codon-optimized for high level expression in a human cell, and wherein the sequence of nucleotides that encodes the human HER2ECDTM comprises SEQ ID NO:9.

2. A vector comprising the nucleic acid molecule of claim 1.

3. An isolated host cell comprising the vector of claim 2.

4. A process for expressing a human HER2ECDTM protein in a recombinant host cell, comprising:
(a) introducing a vector comprising the nucleic acid of claim 1 into a suitable isolated host cell; and,
(b) culturing the isolated host cell under conditions which allow expression of said human HER2ECDTM protein.

* * * * *